United States Patent
Funada et al.

(10) Patent No.: US 11,053,516 B2
(45) Date of Patent: Jul. 6, 2021

(54) GLUCOSE COMPOSITION, MICROBIAL FERMENTATION RAW MATERIAL, AND METHOD OF PRODUCING CHEMICAL PRODUCT

(71) Applicant: Toray Industries, Inc., Tokyo (JP)

(72) Inventors: Shigeyuki Funada, Kamakura (JP); Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/082,965

(22) PCT Filed: Mar. 8, 2017

(86) PCT No.: PCT/JP2017/009163
§ 371 (c)(1),
(2) Date: Sep. 7, 2018

(87) PCT Pub. No.: WO2017/154955
PCT Pub. Date: Sep. 14, 2017

(65) Prior Publication Data
US 2019/0100776 A1   Apr. 4, 2019

(30) Foreign Application Priority Data

Mar. 9, 2016 (JP) .............................. JP2016-045147

(51) Int. Cl.
| | |
|---|---|
| *C12P 7/46* | (2006.01) |
| *C12P 1/00* | (2006.01) |
| *C12P 7/06* | (2006.01) |
| *C12N 1/20* | (2006.01) |
| *C12P 7/56* | (2006.01) |
| *C12P 13/08* | (2006.01) |
| *C12N 1/16* | (2006.01) |
| *C12N 1/00* | (2006.01) |
| *C12P 1/02* | (2006.01) |
| *C12P 1/04* | (2006.01) |
| *C12P 13/00* | (2006.01) |

(52) U.S. Cl.
CPC .................. *C12P 7/06* (2013.01); *C12N 1/00* (2013.01); *C12N 1/16* (2013.01); *C12N 1/20* (2013.01); *C12P 1/00* (2013.01); *C12P 1/02* (2013.01); *C12P 1/04* (2013.01); *C12P 7/46* (2013.01); *C12P 7/56* (2013.01); *C12P 13/08* (2013.01); *C12P 13/00* (2013.01); *Y02E 50/10* (2013.01)

(58) Field of Classification Search
CPC .... C12P 7/06; C12P 1/00; C12P 13/00; C12P 7/46; C12P 1/04; C12P 1/02; C12P 13/08; C12P 7/56; C12N 1/00; C12N 1/16; C12N 1/20; Y02E 50/17
See application file for complete search history.

(56) References Cited

U.S. PATENT DOCUMENTS

| | | |
|---|---|---|
| 2011/0250637 A1 | 10/2011 | Kurihara et al. |
| 2013/0344543 A1 | 12/2013 | Kurihara et al. |
| 2014/0178937 A1 | 6/2014 | Minamino et al. |
| 2014/0287461 A1 | 9/2014 | Kurihara et al. |
| 2018/0142271 A1 | 5/2018 | Isobe et al. |

FOREIGN PATENT DOCUMENTS

| | | |
|---|---|---|
| CN | 101935618 A | 1/2011 |
| EP | 2682472 A1 | 1/2014 |
| EP | 3309259 A1 | 12/2016 |
| JP | 3041380 B2 | 5/2000 |
| WO | 2010/067785 A1 | 6/2010 |
| WO | 2012/118171 | 9/2012 |
| WO | 2013/018694 A1 | 2/2013 |
| WO | 2016/199856 A1 | 12/2016 |
| WO | 2016/199858 A1 | 12/2016 |

OTHER PUBLICATIONS

Filannino et al., Applied and Environmental Microbiology, 2014, vol. 80, No. 24, p. 7574-7582, and Supplemental Table S1.*
Xu et al., Analytica Chimica Acta, 2005, vol. 522, p. 207-217.*
Karatzos et al., Biotechnology for Biofuels, 2012, 5: 62, p. 1-12.*
Sato et al., Applied and Environmental Microbiology, 2014, vol. 80, No. 2, p. 540-554, and supplementary Fig S1.*
A. Aden et al., "Lignocellulosic Biomass to Ethanol Process Design and Economics Utilizing Co-Current Dilute Acid Prehydrolysis and Enzymatic Hydrolysis for Corn Stover," *NREL Technical Report* (2002).
Van der Pol, E. et al., "Analysis of by-product formation and sugar monomerization in sugarcane bagasse pretreated at pilot plant scale: Differences between autohydrolysis, alkaline and acid pretreatment," *Biores. Technol.*, 2015, vol. 181, pp. 114-123.
Martinez, A. et al., "Effects of Ca(OH)2 Treatments "Overliming" on the Composition and Toxicity of Bagasse Hemicellulose Hydrolysates," *Biotechnol. Bioeng.*, 2000, vol. 69, No. 5, pp. 526-536.
White, J.W., "Spectrophotometric method for hydroxymethylfurfural in honey," *J. Assoc. Off. Anal. Chem.*, 1979, vol. 62, No. 3, pp. 509-514.
van der Pol, E. C. et al., "By-products resulting from lignocellulose pretreatment and their inhibitory effect on fermentations for (bio)chemicals and fuels," *Appl. Microbiol. Biotechnol.*, 2014, vol. 98, pp. 9579-9593.
Taherzadeh, M.J. et al., "Acetic acid-friend or foe in anaerobic batch conversion of glucose to ethanol by *Saccharomyces cerevisiae?*" *Chem. Eng. Sci.*, 1997, vol. 52, No. 15, pp. 2653-2659.

(Continued)

*Primary Examiner* — Kade Ariani
(74) *Attorney, Agent, or Firm* — DLA Piper LLP (US)

(57) ABSTRACT

A glucose composition contains, as equivalents in an aqueous solution of the composition having a glucose concentration of 100 g/L, 0-25 g/L of xylose, 0.1-10 g/L of acetic acid, 0.15-2.0 g/L of coumaric acid, and 0.007-0.28 g/L of ferulic acid. By using this glucose composition as a raw material in a method for producing a chemical product by microbial fermentation, the yield of the chemical product can be raised.

9 Claims, No Drawings

(56) References Cited

OTHER PUBLICATIONS

Guo, W. et al., "Performances of Lactobacillus brevis for Producing Lactic Acid from Hydrolysate of Lignocellulosics," *Appl. Biochem. Biotechnol.*, 2010, vol. 161, pp. 124-136.

Cao, D. et al., "Inhibitory Activity of Carbonyl Compounds on Alcoholic Fermentation by *Saccharomyces cerevisiae*," *J. Agric. Food Chem.*, 2014, vol. 62, pp. 918-926.

Yoshikuni, T. et al., "Geometrical consideration for meta-cresol and the oxidative products in chemical section of high school education," Faculty of Education, Gunma University Kiyo Shizen Kagaku Hen, 2009, vol. 57, pp. 63-71 [Concise Statement of Relevance in English is provided].

Ezeji, T. et al., "Butanol Production from Agricultural Residues: Impact of Degradation Products on Clostridium beijerinckii Growth and Butanol Fermentation", *Biotechnol. Bioeng.*, 2007, vol. 97, No. 6, pp. 1460-1469.

Favaro, L. et al., "Exploring grape marc as trove for new thermotolerant and inhibitor-tolerant *Saccharomyces cerevisiae* strains for second-generation bioethanol production," *Biotechnol. Biofuel.*, 2013, vol. 6, art. No. 168(pp. 1-14).

De Assis Castro, R.C. and Roberto, I.C., "Effect of nutrient supplementation on ethanol production in different strategies of saccharification and fermentation from acid pretreated rice straw," *Biomass Bioenergy*, 2015, vol. 78, pp. 156-163.

Guo, T. et al., "Clostridium beijerinckii mutant with high inhibitor tolerance obtained by low-energy ion implantation," *J. Ind. Microbiol. Biotechnol.*, 2012, vol. 39, pp. 401-407.

Martin, C. et al., "Ethanol production from enzymatic hydrolysates of sugarcane bagasse using recombinant xylose-utilising *Saccharomyces cerevisiae*," *Enzyme Microb. Technol.*, 2002, vol. 31, pp. 274-282.

Martinez, A. et al., "Use of UV Absorbance to Monitor Furans in Dilute Acid Hydrolysatos of Biomass," *Biotechnol. Prog.*, 2000, vol. 16, pp. 637-641.

Van der Pol, E.C. et al., "Identifying inhibitory effects of lignocellulosic by-products on growth of lactic acid producing microorganisms using a rapid small-scale screening method," *Biores. Technol.*, Mar. 11, 2016, vol. 209, pp. 297-304.

Extended European Search Report dated Aug. 7, 2019, of counterpart European Application No. 17763295.7.

Office Action dated Jan. 20, 2021, of counterpart Indian Application No. 201847033713.

Office Action dated Apr. 6, 2021, of counterpart Japanese Application No. 2017-515251 along with an English translation.

Adeboye, P.T. et al., "Catabolism of coniferyl aldehyde, ferulic acid and p-coumaric acid by *Saccharomyces cerevisiae* yields less toxic products," *Microb. Cell Fact.*, 2015, vol. 14, article 149, pp. 1-14.

Adeboye, P.T. et al., "The chemical nature of phenolic compounds determines their toxicity and induces distinct physiological responses in *Saccharomyces cerevisiae* in lignocellulose hydrolysates," *AMB Express*, 2014, vol. 4, article 45, pp. 2-13.

Verduyn C. et al. "Effect of Benzoic Acid on Metabolic Fluxes in Yeasts: A Continuous-Culture Study on the Regulation of Respiration and Alcoholic Fermentation," *Yeast*, 1992, vol. 8, pp. 501-517.

First Office Action dated Mar. 31, 2021, of counterpart Chinese Application No. 201780015538.1 along with an English translation.

\* cited by examiner

GLUCOSE COMPOSITION, MICROBIAL FERMENTATION RAW MATERIAL, AND METHOD OF PRODUCING CHEMICAL PRODUCT

TECHNICAL FIELD

This disclosure relates to a glucose composition and a microbial fermentation raw material, each of which enhances microbial fermentation efficiency, and a method of producing a chemical product by microbial fermentation.

BACKGROUND

A fermentation production process for a chemical product using a sugar as a raw material has been used in the production of various industrial raw materials. As the sugar to serve as this fermentation raw material, currently, a sugar derived from an edible raw material such as sugarcane, starch, or sugar beets is industrially used. An unrefined sugar obtained from sugarcane or sugar beets is a sugar solution in which sucrose is contained as a main component and the sucrose purity is as high as 95% or more. On the other hand, a mother liquor produced after crystallization in the process of obtaining the unrefined sugar is on the market as waste molasses, which is a mixture of sucrose, glucose, and fructose, and contains various salts, proteins and the like as impurities and, therefore, is a sugar solution in which the total concentration of various sugars such as sucrose, glucose, and fructose is 50% or so and the amount of impurities other than sugars is large. Starch obtained from corn, wheat, cassava or the like is converted into glucose using an enzyme, followed by purification and concentration, whereby a sugar solution in which the glucose purity is as high as 98% or more is produced.

Aside from the sugar produced from an edible resource described above, from the viewpoint of a steep rise in the price of an edible raw material due to an increase in global population in future or from an ethical viewpoint of competition with foods, sugar production using a recyclable non-edible resource, that is, cellulose-containing biomass as a raw material has also been developed. As a method of producing a sugar solution from cellulose-containing biomass, a method of producing a sugar solution by acid hydrolysis of cellulose and hemicellulose using concentrated sulfuric acid, and a method of producing a sugar solution by subjecting cellulose-containing biomass to a hydrolysis treatment with dilute sulfuric acid, and thereafter further subjecting the resulting material to an enzymatic treatment using cellulase or the like are known (A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report (2002)). Also, a method of producing a sugar solution by subjecting cellulose-containing biomass to a hydrolysis treatment with pressurized hot water at 240 to 280° C. and, thereafter, further subjecting the resulting material to an enzymatic saccharification treatment (Japanese Patent No. 3041380) is disclosed. However, a sugar using cellulose-containing biomass as a raw material contains xylose which is a low fermentable pentose other than glucose, and further contains an organic acid such as acetic acid, HMF (hydroxymethylfurfural), coumaric acid, ferulic acid, vanillin and the like as fermentation inhibitors and, therefore, the method had a problem that the fermentation yield is low when it is used as a microbial fermentation raw material. As a method of solving the problem, a method of producing a sugar solution by passing a sugar solution containing fermentation inhibitors obtained by subjecting a cellulose-containing biomass raw material to a treatment with pressurized hot water, followed by hydrolysis with cellulase through an ultrafiltration membrane, a nanofiltration membrane, or a reverse osmosis membrane, thereby removing the fermentation inhibitors and the like, are known (WO 2010/067785 and WO 2013/018694).

A microbial fermentation raw material produced using a sugar as a main raw material generally needs a configuration in accordance with the nutritional rule. A solid material of cells contains hydrogen and oxygen that can be supplied from water or air, and in addition thereto, carbon, nitrogen, phosphorus, and sulfur, which are listed in descending order of amount, and the total amount of these elements corresponds to 95% of the dry weight of cells. The remaining 5% contains many mineral elements. In addition thereto, as materials that cannot be biosynthesized using a simple carbon source and are required to be added to a culture medium, growth factors such as amino acids, purine, pyrimidine, and vitamins can be cited. However, as for the amounts thereof, only small amounts are required. That is, a microbial fermentation raw material is prepared to supply a carbon source using such as a carbohydrate which is a sugar as the most major component, a nitrogen source using such as yeast extract, corn steep liquor (CSL), and ammonia salt and the like to a microorganism.

As described above, as a sugar to serve as a microbial fermentation raw material, there exist a sugar derived from an edible raw material, a sugar derived from cellulose-containing biomass and the like, and a culture medium for fermentation is prepared using such a sugar. However, a sugar composition capable of obtaining higher fermentation efficiency has been demanded from the industrial world. Therefore, it could be helpful to provide a glucose composition capable of obtaining higher fermentation efficiency than that obtained with a conventional sugar composition.

SUMMARY

We surprisingly found that a glucose composition containing specific amounts of acetic acid, coumaric acid, and ferulic acid, which are known as fermentation inhibitors favorable as a microbial fermentation raw material.

We thus provide:

[1] A glucose composition containing 0 to 25 g/L of xylose, 0.1 to 10 g/L of acetic acid, 0.15 to 2.0 g/L of coumaric acid and 0.007 to 0.28 g/L of ferulic acid, as equivalents in an aqueous solution of the composition having a glucose concentration of 100 g/L.

[2] The glucose composition according to [1], containing a substance obtained by subjecting a bagasse to an alkali treatment and has an absorption at 280 nm measured in a 1-cm width cell at a concentration defined by an absorbance (ABS) of 20 to 350 as an equivalent in an aqueous solution of the glucose composition having a glucose concentration of 100 g/L.

[3] A glucose composition for a microbial fermentation, containing the glucose composition according to [1] or [2].

[4] A microbial fermentation raw material containing the glucose composition according to [1] or [2], or the glucose composition for a microbial fermentation according to [3].

[5] A method of producing a chemical product, comprising culturing a microorganism having an ability to produce the chemical product by using the microbial fermentation raw material according to [4].

When our glucose composition is used as a microbial fermentation raw material, higher fermentation efficiency than that obtained with a conventional sugar composition can be obtained, and the production cost of a chemical product by fermentation production of the chemical product using a sugar as a raw material can be reduced.

DETAILED DESCRIPTION

Our raw materials, compositions and methods will be described in detail.

Glucose Composition

As glucose which is a main component of the glucose composition, high-purity glucose produced by enzymatic hydrolysis from starch using corn, wheat, cassava or the like as a raw material can be used. As described below, glucose obtained by appropriately hydrolyzing cellulose-containing biomass can also be used.

As xylose contained in the glucose composition, xylose is contained much in corn cobs or the like, and can be obtained by purification thereof. Also, as described below, xylose obtained by appropriately hydrolyzing cellulose-containing biomass can also be used.

As acetic acid, acetic acid obtained from a raw material derived from petroleum such as carbonylation of methanol, or acetic acid obtained by fermentation production using a microorganism of the genus *Acetobacter* or the like can be used. Also, as described below, acetic acid is contained as an accessory component when producing a sugar such as glucose by hydrolyzing cellulose-containing biomass, and therefore may be cellulose-containing biomass-derived acetic acid.

Coumaric acid and ferulic acid are each one of the constituent components of lignin in a plant, and can be produced by purification from a plant raw material or the like or by chemical synthesis from a petroleum-derived raw material. Further, in the same manner as acetic acid, coumaric acid and ferulic acid are contained as accessory components when producing a sugar such as glucose by hydrolyzing cellulose-containing biomass and, therefore, may be cellulose-containing biomass-derived coumaric acid and ferulic acid. There are three types of isomers of coumaric acid, o-coumaric acid, m-coumaric acid, and p-coumaric acid, and coumaric acid contained in the glucose composition may be any of the isomers, or a mixture of two or more types thereof. However, p-coumaric acid abundantly exists in nature as one of the constituent components of lignin, and therefore, coumaric acid is preferably p-coumaric acid or a mixture containing p-coumaric acid as a main component. Further, p-coumaric acid exists in the cis-form and the trans-form and may be in either form or a mixture of these two forms. However, p-coumaric acid stably exists in the trans-form in a state of nature where it is not exposed to light, and therefore, it is preferably trans-p-coumaric acid.

The glucose composition can be prepared by appropriately dissolving or mixing the compounds to serve as constituent components in a solvent. For example, the glucose composition can be produced by sufficiently purifying the substances and, thereafter, mixing the substances so that the xylose concentration is 0 to 25 g/L, preferably 0.5 to 25 g/L, the acetic acid concentration is 0.1 to 10 g/L, preferably 0.2 to 4 g/L, the coumaric acid concentration is 0.15 to 2.0 g/L, preferably 0.3 to 1.0 g/L, and the ferulic acid concentration is 0.007 to 0.28 g/L, preferably 0.014 to 0.14 g/L in an aqueous solution having a glucose concentration of 100 g/L. The dissolving or mixing order is not particularly limited, and the pH, temperature or the like may be appropriately adjusted. When the glucose composition is dissolved in a solvent, the glucose and xylose concentrations can be quantitatively determined by an RI detector using high performance liquid chromatography (HPLC), the coumaric acid and ferulic acid concentrations can be quantitatively determined by a UV detector or a photodiode array similarly using high performance liquid chromatography, and acetic acid can be quantitatively determined by an electric conductivity meter similarly using high performance liquid chromatography.

The glucose composition may be produced using cellulose-containing biomass as a raw material and, for example, after cellulose-containing biomass is subjected to a pretreatment such as an alkali treatment, a solid after solid-liquid separation is subjected to hydrolysis with a saccharification enzyme such as filamentous fungus-derived cellulase, then the obtained aqueous sugar solution is purified so that the concentrations of the constituent components of the glucose composition are predetermined values to perform production, whereby the glucose composition can be obtained at a lower cost than by mixing all sorts of necessary purified products.

The cellulose-containing biomass refers to a biological resource containing 5 mass % or more of cellulose. Specifically, herbaceous biomass such as bagasse, switch grass, napier grass, erianthus, corn stover, rice straws, and wheat straws, woody biomass such as trees and waste construction materials and the like can be mentioned as examples. These cellulose-containing biomass contains lignin which is an aromatic polymer, cellulose and hemicellulose, and therefore is also referred to as lignocellulose. By hydrolyzing cellulose and hemicellulose which are polysaccharide components contained in the cellulose-containing biomass, a sugar solution containing xylose and glucose can be obtained.

The cellulose-containing biomass is preferably bagasse. The bagasse is a residue after cane juice is squeezed out by compressing sugarcane stalks, and has a water content of 40 to 50%, and contains 35 to 45% (wt/wt dry bagasse) of cellulose, 20 to 28% (wt/wt dry bagasse) of xylose, and 3 to 20% (wt/wt dry bagasse) of lignin. It is only necessary that the above-mentioned cellulose, xylose, and lignin are contained in bagasse, and the type of sugarcane is not particularly limited.

Specific examples of the pretreatment of the cellulose-containing biomass include an alkali treatment in which a treatment is performed with an alkaline aqueous solution of calcium hydroxide, sodium hydroxide or the like; an acid treatment in which a treatment is performed with dilute sulfuric acid, a sulfite, or the like at high temperature and high pressure; and a hydrothermal treatment in which a treatment is performed with pressurized hot water. The pretreatment is preferably performed by an alkali treatment.

The saccharification enzyme is preferably filamentous fungus-derived cellulase, and as the filamentous fungus, microorganisms of the genus *Trichoderma* (*Trichoderma*), the genus *Aspergillus* (*Aspergillus*), the genus *Cellulomonas* (*Cellulomonas*), the genus *Clostridium* (*Chlostridium*), the genus *Streptomyces* (*Streptomyces*), the genus *Humicola* (*Humicola*), the genus *Acremonium* (*Acremonium*), the genus *Irpex* (*Irpex*), the genus *Mucor* (*Mucor*), the genus *Talaromyces* (*Talaromyces*), and the like can be exemplified. Among the filamentous fungi, a microorganism of the genus *Trichoderma* produces a large amount of an enzymatic component having a high specific activity in the hydrolysis of cellulose in a culture solution, and therefore can be preferably used.

As the method of preparing the glucose composition by purifying the aqueous sugar solution, a method in which the aqueous sugar solution is filtered through a separation membrane with a molecular weight cutoff of 300 to 1,000, preferably 300 to 500 and collected as a permeate is exemplified. Specific examples of the separation membrane include NFW (molecular weight cutoff: 300 to 500), NFG (molecular weight cutoff: 600 to 800), and NDX (molecular weight cutoff: 800 to 1,000) of Synder Filtration, Inc. and the like.

In the glucose composition, a substance other than the above-mentioned xylose, acetic acid, coumaric acid, and ferulic acid may be contained as long as it does not inhibit the desired effect and, for example, when the glucose composition is produced by employing cellulose-containing biomass as a raw material and using bagasse, a substance having absorption at 280 nm measured in a 1-cm width cell may be contained. This substance is presumed to be a component derived from lignin in bagasse, and although the chemical structure has not been specified because it has a complicated structure, the substance has a characteristic that it has absorption at 280 nm which is in an ultraviolet range due to having an aromatic ring, and the concentration of this substance is proportional to the absorbance at 280 nm. When this substance is contained in the glucose composition, the content thereof is not particularly limited as long as it does not inhibit the desired effect. However, by containing this substance at a concentration defined by an absorbance (ABS) of 20 to 350 as an equivalent in an aqueous solution having a glucose concentration of 100 g/L, the fermentation yield by microbial fermentation can be further enhanced.

The substance having absorption at 280 nm measured in a 1-cm width cell described above is contained in an aqueous sugar solution obtained by hydrolyzing bagasse with a saccharification enzyme and, therefore, this substance may be mixed by appropriately mixing the aqueous sugar solution in the glucose composition prepared without using cellulose-containing biomass as a raw material.

The form of the glucose composition is not particularly limited as long as specific amounts of the substances other than glucose specified as described above are contained in the aqueous solution of the composition obtained by dissolving the composition in water so that the glucose concentration is 100 g/L, and it may be adjusted to various glucose concentrations by concentration or dilution as appropriate. However, by setting the glucose concentration to 600 g/L or more in the form of an aqueous solution, the water activity can be kept low, the consumption of the sugar by contamination with a microorganism can be prevented and, thus, the storage stability can be enhanced.

Glucose Composition for Microbial Fermentation

The use of the glucose composition is not particularly limited, however, the microbial fermentation efficiency can be enhanced as compared to when only glucose is used and, therefore, the composition can be favorably used for microbial fermentation. Specifically, when the glucose composition is used for microbial fermentation, an excellent effect on the fermentation efficiency, specifically the fermentation rate, the fermentation yield versus the theoretical ratio, the fermentation yield versus the consumed sugar ratio, or the microbial growth potential can be obtained.

The fermentation rate is a rate at which the concentration of a fermentation product increases per unit time. In the fermentation rate, the initial rate is high, and the rate approaches 0 as the fermentation reaches the final stage at which the sugar is consumed. As the fermentation rate, a value measured at 12 to 24 hours after the start of fermentation is used.

The fermentation yield versus the theoretical ratio is defined as the ratio of the concentration at which the product is actually produced to the concentration of the product that can be theoretically obtained for a fermentation production microorganism based on the decreased amount of the sugar. The product which can be theoretically obtained is 0.51 g of ethanol/g of the consumed sugar in ethanol fermentation, 1.0 g of lactic acid/g of the consumed sugar in lactic acid fermentation, and 0.66 g of succinic acid/g of the consumed sugar for *Actinobacillus Succinogenes* although it depends on the strain to be examined in succinic acid fermentation.

The fermentation yield versus the consumed sugar ratio is defined as the ratio of the concentration at which the product is produced to the decreased concentration of the sugar. For example, when only glucose is consumed as the sugar raw material, it is referred to as the fermentation yield versus the consumed glucose ratio.

The microbial growth potential is quantitatively determined by a numerical value measured as the OD value of a fermentation culture solution. The OD value is determined to be an absorbance at 600 nm of visible light, and can be measured by a spectrophotometer for an analysis using a 1-cm width cell.

When the glucose composition contains xylose, the assimilability of xylose varies depending on the microorganism to be used in fermentation. Accordingly, for example, when using yeast not having an ability to assimilate xylose, xylose is incorporated in a small amount in the microorganism by the action of a hexose transporter or the like, but is not assimilated and, therefore, the fermentation yield versus the theoretical ratio is lowered. However, in the glucose composition containing xylose, acetic acid, coumaric acid, and ferulic acid, incorporation of xylose into the microorganism is suppressed and, as a result, the rate of fermentation and the fermentation yield versus the theoretical ratio in which glucose metabolism mainly occurs, can be improved. In a microorganism having an ability to assimilate xylose, by containing acetic acid, coumaric acid, and ferulic acid, conversion from xylose to a product is accelerated, and the fermentation rate and the fermentation yield versus the theoretical ratio can be improved.

Microbial Fermentation Raw Material

The glucose composition can be used as a microbial fermentation raw material by itself, but a microbial fermentation raw material in which an auxiliary raw material is appropriately added for the purpose of supplying a nitrogen source or a vitamin according to the type of the microorganism to be used for fermentation production may also be prepared. Examples of the auxiliary raw material include components derived from a natural product such as yeast extract, peptone, or corn steep liquor (CSL), minerals, vitamins and the like.

The glucose concentration when the glucose composition is used as the microbial fermentation raw material is not particularly limited, but is preferably 10 to 200 g/L. Only glucose and xylose may be added at a stage where glucose and xylose have been consumed.

Method of Producing Chemical Product

By culturing a microorganism that produces a desired chemical product using the microbial fermentation raw material containing the glucose composition, the desired chemical product can be produced.

The method of culturing a microorganism is not particularly limited, and the culture can be performed according to a known fermentation culture method. However, a continuous culture method disclosed in WO 2007/097260 is preferably adopted from the viewpoint of productivity.

As the microorganism that can produce a chemical product by fermentation using the glucose composition as a fermentation raw material, specifically, yeast, lactic acid bacteria, succinic acid-producing bacteria, *Escherichia coli*, alcohol fermentation bacteria, organic acid fermentation bacteria, amino acid fermentation bacteria and the like are exemplified. However, preferred microorganisms are yeast, lactic acid bacteria, and succinic acid-producing bacteria. These microorganisms may be those isolated from a natural environment or those obtained by partially modifying the properties by mutation or gene recombination.

As the chemical product, a substance mass-produced in fermentation industry such as an alcohol, an organic acid, an amino acid, or a nucleic acid can be exemplified. For example, alcohols such as ethanol, 1,3-propanediol, 1,4-butandiol, and glycerol, organic acids such as lactic acid, succinic acid, pyruvic acid, malic acid, itaconic acid, and citric acid, nucleosides such as inosine and guanosine, nucleotides such as inosinic acid and guanylic acid, amino acids such as lysine, glutamic acid, tryptophan, valine, threonine, aspartic acid, alanine, ormithine, and aminolevulinic acid, and amine compounds such as cadaverine can be exemplified. Further, it can also be applied to the production of an enzyme, an antibiotic, a recombinant protein and the like. The chemical product to be produced by fermentation is preferably ethanol, lactic acid, succinic acid, lysine, and cadaverine.

As the yeast that can produce the above-mentioned chemical products by fermentation, specifically, for example, *Saccharomyces cerevisiae* (*Saccharomyces cerevisiae*), *Schizosaccharomyces pombe* (*Schizosaccharomyces pombe*), *Pichia stipitis* (*Pichia stipitis*), *Candida shehatae* (*Candida shehatae*), *Candida glabrata* (*Candida glabrata*) and the like are exemplified.

As the lactic acid bacteria, specifically, for example, microorganisms belonging to the genus *Lactobacillus* (*Lactobacillus*) and the genus *Lactococcus* (*Lactococcus*) and the like are exemplified and, more specifically, *Lactobacillus plantarum* (*Lactobacillus plantarum*), *Lactobacillus casei* (*Lactobacillus casei*), *Lactobacillus sakei* (*Lactobacillus sakei*), *Lactococcus lactis* (*Lactococcus lactis*), *Bacillus coagulans* (*Bacillus coagulans*) and the like are exemplified.

As the succinic acid-producing bacteria, specifically, for example, *Actinobaccillus succinogenes* (*Actinobaccillus succinogenes*), *Corynebacterium glutamicum* (*Corynebacterium glutamicum*) and the like are exemplified.

As the lysine-producing bacteria, *Escherichia coli* (*Escherichia coli*), coryneform bacteria and the like are exemplified. As specific examples of *Escherichia coli*, MC1061 strain, HB101 strain, JM105 strain, JM109 strain, DH5α strain, JE5505 strain and the like can be used. The coryneform bacteria are Gram-positive aerobic bacilli and had been conventionally classified into the genus *Brevibacterium*, but now also include bacteria which are integrated into the genus *Corynebacterium* (Int. J. Syst., Bacteriol., (1981) 41, p. 225). In addition, bacteria of the genus *Brevibacterium* very closely relative of the genus *Corynebacterium* are included. Examples of such coryneform bacteria include *Corynebacterium acetoacidophylum* (*Corynebacterium acetoacidophylum*), *Corynebacterium acetoglutamicum* (*Corynebacterium acetoglutamicum*), *Corynebacterium alkanolyticum* (*Corynebacterium alkanolyticum*), *Corynebacterium callunae* (*Corynebacterium callunae*), *Corynebacterium glutamicum* (*Corynebacterium glutamicum*), *Corynebacterium lilium* (*Corynebacterium lilium*), *Corynebacterium mellassecola* (*Corynebacterium mellassecola*), *Corynebacterium thermoaminogenes* (*Corynebacterium thermoaminogenes*), *Corynebacterium efficiens* (*Corynebacterium efficiens*), *Corynebacterium herculis* (*Corynebacterium herculis*), *Brevibacterium divaricatum* (*Brevivacterium divaricatum*), *Brevibacterium flavum* (*Brevivacterium flavum*), *Brevibacterium immariophilum* (*Brevivacterium immariophilum*), *Brevibacterium lactofermentum* (*Brevivacterium lactofermentum*), *Brevibacterium roseum* (*Brevivacterium roseum*), *Brevibacterium saccharolyticum* (*Brevivacterium saccharolyticum*), *Brevibacterium thiogenitalis* (*Brevivacterium thiogenitalis*), *Corynebacterium ammoniagenes* (*Corynebacterium ammoniagenes*), *Brevibacterium album* (*Brevivacterium album*), *Brevibacterium cerinum* (*Brevivacterium cerinum*), and *Microbacterium ammoniaphilum* (*Microbacterium ammoniaphilum*).

EXAMPLES

Hereinafter, our raw materials, compositions and methods will be specifically described by Examples. However, this disclosure is not limited thereto.

Reference Example 1: Preparation of Yeast (*Saccaromyces cereveciae*) to be Used in Ethanol Fermentation Evaluation Test As an ethanol fermentation microorganism, *Saccharomyces cerevisiae* (*Saccharomyces cereveciae*) (wine yeast OC2 strain, NBRC 2260) was used. 2 mL of YPD medium (prepared to contain 20 g/L of peptone, 10 g/L of yeast extract, and 10 g/L of glucose after separately sterilizing peptone, a yeast extract concentrate, and a glucose concentrate by autoclaving at 121° C. for 20 minutes) was placed in a test tube, and in a clean bench, a colony of the yeast formed by plate culture (30° C., 1 to 2 days) on YPD agar medium was inoculated therein using a platinum loop. This was subjected to reciprocal shaking culture with an inclination of 50° at 30° C. and 120 rpm for 24 hours using a shaker (BIO-SHAKER BR-40LF, manufactured by TAITEC CORPORATION), whereby a preculture solution was obtained. The preculture solution was centrifuged at 15,000×g for 5 minutes at 4° C., and the supernatant was removed and, thereafter, the residue was suspended in 2 mL of a saline solution, whereby a precultured bacterial cell solution with an OD of 7.5 was obtained.

Reference Example 2: Measurement of Sugar and Ethanol Concentrations

The concentrations of glucose and xylose contained in the sugar solution, and the concentration of ethanol produced by fermentation were quantitatively determined under the following HPLC conditions compared to a reference standard:
Column: Shodex SH1011 (manufactured by Showa Denko K. K.)
Mobile phase: 5 mM sulfuric acid (flow rate: 0.6 mL/min)
Reaction solution: None
Detection method: RI (differential refractive index)
Temperature: 65° C.

Example 1: Preparation of Glucose Composition and Ethanol Fermentation Production A glucose composition was prepared by dissolving glucose (D(+)-glucose, manufactured by Wako Pure Chemical Industries, Ltd.) at 100 g/L, acetic acid (reagent special grade, 99.7%, manufactured by Wako Pure Chemical Industries, Ltd.) at 0.1 g/L, coumaric acid (trans-p-coumaric acid, manufactured by Tokyo Chemical Industry Co., Ltd.) at 0.15 g/L, and ferulic acid (trans-ferulic acid, manufactured by Tokyo Chemical Industry Co., Ltd.) at 0.007 g/L in pure water. Coumaric acid and ferulic acid are not dissolved under acidic conditions and, therefore, a 1 g/L concentrate of each component with a pH of 8 was prepared using a 6 N aqueous sodium hydroxide solution, and the glucose composition was prepared by diluting the concentrates. Further, the glucose composition was adjusted to a final pH of 7 using 6 N sodium hydroxide.

To 9 mL of the prepared glucose composition, a 1 mL of a 20% CSL (manufactured by Oji Cornstarch Co., Ltd., after the pH was adjusted to 5 with 1 N NaOH, filter sterilization was performed through a filter with an average pore diameter of 0.45 μm) solution was added as a nitrogen source, and the precultured bacterial cells described in Reference Example 1 were inoculated therein to an initial OD of 0.5. This was subjected to reciprocal shaking culture with an inclination of 50° at 30° C. and 120 rpm for 144 hours. Sampling was performed about every 24 hours, and the sugar concentration and the ethanol concentration were analyzed, and the maximum fermentation rate and the fermentation yield versus the theoretical ratio (the ratio to theoretical value when the theoretical yield of ethanol was assumed to be 0.51 g/g—the total consumed sugar) were determined. As the evaluation of microbial growth potential, the OD (OD600) of the culture solution after 48-hour culture was measured. The results are shown in Table 1.

Example 2: Preparation of Glucose Composition and Ethanol Fermentation Production The same procedure as in Example 1 was performed except that a glucose composition containing 100 g/L of glucose, 0.7 g/L of xylose (D(+)-xylose, manufactured by Wako Pure Chemical Industries, Ltd.), 0.1 g/L of acetic acid, 0.15 g/L of coumaric acid, and 0.007 g/L of ferulic acid was prepared. The results are shown in Table 1.

Example 3: Preparation of Glucose Composition and Ethanol Fermentation Production The same procedure as in Example 1 was performed except that a glucose composition containing 100 g/L of glucose, 22.3 g/L of xylose, 1 g/L of acetic acid, 0.5 g/L of coumaric acid, and 0.06 g/L of ferulic acid was prepared. The results are shown in Table 1.

Example 4: Preparation of Glucose Composition and Ethanol Fermentation Production The same procedure as in Example 1 was performed except that a glucose composition containing 100 g/L of glucose, 25 g/L of xylose, 10 g/L of acetic acid, 2 g/L of coumaric acid, and 0.28 g/L of ferulic acid was prepared. The results are shown in Table 1.

Comparative Example 1: Comparative Example of Glucose Composition in Ethanol Fermentation Production The same procedure as in Example 1 was performed except that a glucose composition containing only 100 g/L of glucose was prepared. The results are shown in Table 1.

Comparative Example 2: Comparative Example of Glucose Composition in Ethanol Fermentation Production The same procedure as in Example 1 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 1.

Comparative Example 3: Comparative Example of Glucose Composition in Ethanol Fermentation Production The same procedure as in Example 1 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 1.

Comparative Example 4: Comparative Example of Glucose Composition in Ethanol Fermentation Production The same procedure as in Example 1 was performed except that a glucose composition containing 100 g/L of glucose, 22.3 g/L of xylose, 1 g/L of acetic acid, 3.0 g/L of coumaric acid, and 0.06 g/L of ferulic acid was prepared. The results are shown in Table 1.

Comparative Example 5: Comparative Example of Glucose Composition in Ethanol Fermentation Production The same procedure as in Example 1 was performed except that a glucose composition containing 100 g/L of glucose, 22.3 g/L of xylose, 1 g/L of acetic acid, no coumaric acid, and 0.06 g/L of ferulic acid was prepared. The results are shown in Table 1.

Comparative Example 6: Comparative Example of Glucose Composition in Ethanol Fermentation Production The same procedure as in Example 1 was performed except that a glucose composition containing 100 g/L of glucose, 22.3 g/L of xylose, 1 g/L of acetic acid, 0.5 g/L of coumaric acid, and 0.4 g/L of ferulic acid was prepared. The results are shown in Table 1.

Comparative Example 7: Comparative Example of Glucose Composition in Ethanol Fermentation Production The same procedure as in Example 1 was performed except that a glucose composition containing 100 g/L of glucose, 22.3 g/L of xylose, 1 g/L of acetic acid, 0.5 g/L of coumaric acid, and no ferulic acid was prepared. The results are shown in Table 1.

Comparative Example 8: Comparative Example of Glucose Composition in Ethanol Fermentation Production The same procedure as in Example 1 was performed except that a glucose composition containing 100 g/L of glucose, 50 g/L of xylose, 1 g/L of acetic acid, 0.5 g/L of coumaric acid, and 0.06 g/L of ferulic acid was prepared. The results are shown in Table 1.

TABLE 1

Ethanol fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus theoretical ratio (%) |
| Example 1 | 100 | 0 | 0.1 | 0.15 | 0.007 | 12.5 | 1.27 | 89 |
| Example 2 | 100 | 0.7 | 0.1 | 0.15 | 0.007 | 12.5 | 1.25 | 89 |
| Example 3 | 100 | 22.3 | 1.0 | 0.5 | 0.06 | 9.1 | 1.42 | 91 |
| Example 4 | 100 | 25 | 10 | 2.0 | 0.28 | 8.5 | 1.25 | 90 |
| Comparative Example 1 | 100 | 0 | 0 | 0 | 0 | 14.9 | 1.17 | 84 |
| Comparative Example 2 | 100 | 22.3 | 15 | 0.5 | 0.06 | 7.5 | 1.10 | 82 |
| Comparative Example 3 | 100 | 22.3 | 0 | 0.5 | 0.06 | 13.5 | 1.15 | 84 |
| Comparative Example 4 | 100 | 22.3 | 1.0 | 3.0 | 0.06 | 8.2 | 0.83 | 81 |
| Comparative Example 5 | 100 | 22.3 | 1.0 | 0 | 0.06 | 9.5 | 1.16 | 84 |
| Comparative Example 6 | 100 | 22.3 | 1.0 | 0.5 | 0.4 | 8.4 | 1.16 | 82 |
| Comparative Example 7 | 100 | 22.3 | 1.0 | 0.5 | 0 | 9.7 | 1.18 | 85 |
| Comparative Example 8 | 100 | 50 | 1.0 | 0.5 | 0.06 | 9.0 | 1.22 | 85 |

Reference Example 3: Method of Preparing Filamentous Fungus-Derived Cellulase (Culture Solution)

A filamentous fungus-derived cellulase (culture solution) was prepared by the following method.
Preculture
The following components were added to distilled water at concentrations as indicated: corn steep liquor (CSL) at 5% (w/vol), glucose at 2% (w/vol), ammonium tartrate at 0.37% (w/vol), ammonium sulfate at 0.14 (w/vol), potassium dihydrogen phosphate at 0.2% (w/vol), calcium chloride dihydrate at 0.03% (w/vol), magnesium sulfate heptahydrate at 0.03% (w/vol), zinc chloride at 0.02% (w/vol), iron(III) chloride hexahydrate at 0.01% (w/vol), copper(II) sulfate pentahydrate at 0.004% (w/vol), manganese chloride tetrahydrate at 0.0008% (w/vol), boric acid at 0.0006% (w/vol), and hexaammonium heptamolybdate tetrahydrate at 0.0026% (w/vol), and 100 mL of the resulting mixture was placed in a 500-mL baffled Erlenmeyer flask and sterilized by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added to the mixture at 0.01% (w/vol) each. In this preculture medium, Trichoderma reesei ATCC 66589 was inoculated at 1×10⁵ cells/mL and cultured with shaking at 180 rpm at a temperature of 28° C. for 72 hours, whereby a preculture was prepared (shaker: BIO-SHAKER BR-40LF, manufactured by TAITEC CORPORATION).
Main Culture
The following components were added to distilled water at concentrations as indicated: corn steep liquor (CSL) at 5% (w/vol), glucose at 2% (w/vol), cellulose (trade name: Avicel, manufactured by Asahi Kasei Chemicals Corporation) at 10% (w/vol), ammonium tartrate at 0.37% (w/vol), ammonium sulfate at 0.14 (w/vol), potassium dihydrogen phosphate at 0.2% (w/vol), calcium chloride dihydrate at 0.03% (w/vol), magnesium sulfate heptahydrate at 0.03% (w/vol), zinc chloride at 0.02% (w/vol), iron(III) chloride hexahydrate at 0.01% (w/vol), copper(II) sulfate pentahydrate at 0.004% (w/vol), manganese chloride tetrahydrate at 0.0008% (w/vol), boric acid at 0.0006% (w/vol), and hexaammonium heptamolybdate tetrahydrate at 0.0026% (w/vol), and 2.5 L of the resulting mixture was placed in a 5-L stirring jar (DPC-2A, manufactured by ABLE Corporation) container and sterilized by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added to the mixture at 0.1% each, and 250 mL of a solution of Trichoderma reesei ATCC 66589 precultured beforehand in the liquid culture medium by the above-mentioned method was inoculated therein. Thereafter, shaking culture was performed at a temperature of 28° C. for 87 hours under the conditions of 300 rpm and an aeration rate of 1 vvm, followed by centrifugation and, then, the supernatant was filtered through a membrane ("Stericup-GV" manufactured by Millipore Corp., material: PVDF). The culture solution prepared under the above-mentioned conditions was used in the following Examples as the filamentous fungus-derived cellulase.

Reference Example 4: Measurement of Cellulase Concentration

The cellulase concentration in an aqueous solution was based on the value of the protein concentration (mg/mL) in an enzyme solution measured by the Bradford method. The protein concentration was measured using a measurement kit (Quick Start Bradford Protein Assay, manufactured by Bio-Rad Laboratories, Inc.) according to the Bradford method.

Example 5: Preparation of Glucose Composition Using Cellulose-Containing Biomass as Raw Material and Ethanol Fermentation Production With respect to 1 kg of the dry weight of bagasse, 30 g of caustic soda which is 5% of the charged amount of the biomass was mixed. Then, reaction at 90° C. for 3 hours was performed, whereby an alkali-treated bagasse was prepared. The alkali-treated bagasse was subjected to solid-liquid separation using a screw press, whereby a solid-liquid separated solid having a water content of 60% was obtained.

The obtained solid-liquid separated solid was resuspended at a solid concentration of 5%, and hydrolyzed with the filamentous fungus-derived cellulase prepared in Reference Example 3 at a protein amount of 8 mg/g-bagasse measured according to Reference Example 4, whereby a glucose composition saccharified solution was obtained. The hydrolysis conditions were set as follows: 40° C., pH 7.0, and a 24-hour reaction time. Solid components were removed from the obtained glucose composition saccharified solution by a screw decanter, and the entire amount of the recovered glucose composition sugar solution was filtered using a microfiltration membrane having a pore diameter of 0.22 μm and, thereafter, the obtained permeate was further subjected to a filtration treatment using an ultrafiltration membrane. As the ultrafiltration membrane, TMUS10k (manufactured by Toray Membrane USA, Inc., material: polyvinylidene fluoride, molecular weight cutoff: 10,000) was used. In the ultrafiltration, a flat sheet membrane filtration unit "SEPA-II" (manufactured by GE Osmonics, Inc.) was used, and the filtration treatment was performed under the conditions that the membrane surface linear velocity was 20 cm/sec and the filtration pressure was 3 MPa until the amount of liquid to be recovered from the non-permeate side reached 0.6 L, whereby a glucose composition saccharified solution was obtained on the permeate side.

The obtained glucose composition saccharified solution was subjected to a filtration treatment through a separation membrane (NFW (material: piperazine polyamide, molecular weight cutoff: 300 to 500), manufactured by Synder Filtration, Inc.). The filtration treatment was performed under the conditions that the membrane surface linear velocity was 20 cm/sec and the filtration pressure was 3 MPa until the concentration rate on the non-permeate side reached 12 times, whereby a glucose composition was obtained on the permeate side.

The obtained glucose composition was concentrated using an evaporator, whereby a glucose composition containing 100 g/L of glucose, 22.3 g/L of xylose, 1.0 g/L of acetic acid, 0.5 g/L of coumaric acid (trans-p-coumaric acid), 0.06 g/L of ferulic acid, and a substance which has absorption at 280 nm measured in a 1-cm width cell at a concentration defined by an absorbance (ABS) of 128 was prepared. Further, the glucose composition was adjusted to a final pH of 7 using 6 N sodium hydroxide.

To 9 mL of the prepared glucose composition, 1 mL of a 20% corn steep liquor (CSL) (manufactured by Oji Cornstarch Co., Ltd., after the pH was adjusted to 5 with 1 N NaOH, filter sterilization was performed through a filter with an average pore diameter of 0.45 μm) solution was added as a nitrogen source, and the precultured bacterial cells (*Saccharomyces cerevisiae* (wine yeast OC2 strain, NBRC 2260)) described in Reference Example 1 were inoculated therein to an initial OD of 0.5. This was subjected to reciprocal shaking culture with an inclination of 50° at 30° C. and 120 rpm for 144 hours. Sampling was performed about every 24 hours, and the sugar concentration and the ethanol concentration were analyzed, and the maximum fermentation rate and the fermentation yield versus the theoretical ratio were determined. As the evaluation of microbial growth potential, the OD (OD600) of the culture solution after 48-hour culture was measured. The results are shown in Table 2.

Example 6: Preparation of Glucose Composition Using Cellulose-Containing Biomass as Raw Material and Ethanol Fermentation Production The same procedure as in Example 5 was performed except that as the separation membrane, UTC-60 (material: piperazine polyamide, molecular weight cutoff: 200 to 250) manufactured by Toray Industries, Inc. was used, whereby a glucose composition containing 100 g/L of glucose, 22.3 g/L of xylose, 1.0 g/L of acetic acid, 0.5 g/L of coumaric acid, 0.06 g/L of ferulic acid, and a substance which has absorption at 280 nm measured in a 1-cm width cell at a concentration defined by an absorbance (ABS) of 12 was prepared. With respect to the prepared glucose composition, ethanol fermentation production was performed in the same manner as in Example 5. The results are shown in Table 2.

Example 7: Preparation of Glucose Composition Using Cellulose-Containing Biomass as Raw Material and Ethanol Fermentation Production The same procedure as in Example 5 was performed except that as the separation membrane, UTC-60 manufactured by Toray Industries, Inc. was used, and to the glucose composition obtained as the permeate, the solid-liquid separated liquid of the alkali-treated bagasse was added at a volume ratio of 1/800, followed by concentration using an evaporator, whereby a glucose composition containing 100 g/L of glucose, 22.3 g/L of xylose, 1.0 g/L of acetic acid, 0.5 g/L of coumaric acid, 0.06 g/L of ferulic acid, and a substance which has absorption at 280 nm measured in a 1-cm width cell at a concentration defined by an absorbance (ABS) of 20 was prepared. Further, the glucose composition was adjusted to a final pH of 7 using 6 N hydrochloric acid. With respect to the prepared glucose composition, ethanol fermentation production was performed in the same manner as in Example 5. The results are shown in Table 2.

Example 8: Preparation of Glucose Composition Using Cellulose-Containing Biomass as Raw Material and Ethanol Fermentation Production The same procedure as in Example 5 was performed except that as the separation membrane, NDX (material: piperazine polyamide, molecular weight cutoff: 800 to 1,000), manufactured by Synder Filtration, Inc. was used, and a glucose composition containing 100 g/L of glucose, 22.3 g/L of xylose, 1.0 g/L of acetic acid, 0.5 g/L of coumaric acid (trans-p-coumaric acid), 0.06 g/L of ferulic acid, and a substance which has absorption at 280 nm measured in a 1-cm width cell at a concentration defined by an absorbance (ABS) of 350 was prepared. With respect to the prepared glucose composition, ethanol fermentation production was performed in the same manner as in Example 5. The results are shown in Table 2.

Example 9: Preparation of Glucose Composition Using Cellulose-Containing Biomass as Raw Material and Ethanol Production The same procedure as in Example 5 was performed except that as the separation membrane, GH series (material:

polyethylene glycol, molecular weight cutoff: 2,500) of GE Company was used, and a glucose composition containing 100 g/L of glucose, 22.3 g/L of xylose, 1.0 g/L of acetic acid, 0.5 g/L of coumaric acid, 0.06 g/L of ferulic acid, and a substance which has absorption at 280 nm measured in a 1-cm width cell at a concentration defined by an absorbance (ABS) of 1,040 was prepared. Further, the glucose composition was adjusted to a final pH of 7 using 6 N hydrochloric acid. With respect to the prepared glucose composition, ethanol fermentation production was performed in the same manner as in Example 5. The results are shown in Table 2.

Industries, Ltd.) at 100 g/L, acetic acid (reagent special grade, 99.7%, manufactured by Wako Pure Chemical Industries, Ltd.) at 0.2 g/L, coumaric acid (trans-p-coumaric acid, manufactured by Tokyo Chemical Industry Co., Ltd.) at 0.3 g/L, and ferulic acid (trans-ferulic acid, manufactured by Tokyo Chemical Industry Co., Ltd.) at 0.014 g/L in pure water. Coumaric acid and ferulic acid are not dissolved under acidic conditions and, therefore, a 1 g/L concentrate of each component with a pH of 8 was prepared using a 6 N aqueous sodium hydroxide solution, and the glucose com-

TABLE 2

Ethanol fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus theoretical ratio (%) |
| Example 5 | 100 | 22.3 | 1.0 | 0.5 | 0.06 | 128 | 9.1 | 1.60 | 95 |
| Example 6 | 100 | 22.3 | 1.0 | 0.5 | 0.06 | 12 | 9.1 | 1.42 | 91 |
| Example 7 | 100 | 22.3 | 1.0 | 0.5 | 0.06 | 20 | 10 | 1.68 | 96 |
| Example 8 | 100 | 22.3 | 1.0 | 0.5 | 0.06 | 350 | 9.0 | 1.60 | 95 |
| Example 9 | 100 | 22.3 | 1.0 | 0.5 | 0.06 | 1040 | 9.0 | 1.40 | 90 |
| Comparative Example 1 | 100 | 0 | 0 | 0 | 0 | 0 | 14.9 | 1.17 | 84 |

Reference Example 5: Preparation of Lactic Acid Bacterium to be Used in Lactic Acid Fermentation Evaluation Test As a lactic acid fermentation microorganism, *Bacillus Coagulans* (*Bacillus Coagulans*) NBRC 12583 strain was used. 2 mL of MRS medium was placed in a test tube, and in a clean bench, a colony of *Bacillus Coagulans* formed by culture on an MRS agar plate (42° C., 1 to 2 days) was inoculated therein using a platinum loop. This was subjected to reciprocal shaking culture with an inclination of 50° at 42° C. and 120 rpm for 24 hours using a shaker (BIO-SHAKER BR-40LF, manufactured by TAITEC CORPORATION), whereby a preculture solution was obtained. The preculture solution was centrifuged at 15,000×g for 5 minutes at 4° C., and the supernatant was removed, and thereafter, the residue was suspended in 2 mL of a saline solution, whereby a precultured bacterial cell solution with an OD of 2.8 was obtained.

Reference Example 6: Measurement of Lactic Acid and Succinic Acid Concentrations The concentrations of lactic acid and succinic acid contained in the sugar solution were quantitatively determined under the following HPLC conditions by comparison with a reference standard:
Column: Shim-Pack SPR-H (manufactured by Shimadzu Corporation)
Mobile phase: 5 mM p-toluenesulfonate (flow rate: 0.8 mL/min)
Reaction solution: 5 mM p-toluenesulfonate, 20 mM bis-Tris, 0.1 mM EDTA.2Na (flow rate: 0.8 mL/min)
Detection method: electric conductivity
Temperature: 45° C.

Example 10: Preparation of Glucose Composition and Lactic Acid Fermentation Production A glucose composition was prepared by dissolving glucose (D(+)-glucose, manufactured by Wako Pure Chemical position was prepared by diluting the concentrates. Further, the glucose composition was adjusted to a final pH of 7 using 6 N sodium hydroxide.
To 4.5 mL of the prepared glucose composition, 5.5 mL of a concentrate obtained by dissolving the following components as auxiliary raw materials such as a nitrogen source at final concentrations as indicated: yeast extract at 10 g/L, ammonium sulfate at 1 g/L, dipotassium hydrogen phosphate at 0.4 g/L, and calcium carbonate at 20 g/L was added, and the precultured bacterial cell solution described in Reference Example 5 was inoculated therein at 1%. This was subjected to static culture at 42° C. for 144 hours. Sampling was performed about every 24 hours, and the sugar concentration and the lactic acid concentration were analyzed by the methods described in Reference Examples 2 and 6, and the maximum fermentation rate and the fermentation yield versus the theoretical ratio (the theoretical ratio when the theoretical yield of lactic acid was assumed to be 1.0 g/g—the total consumed sugar) were determined. As the evaluation of microbial growth potential, the OD (OD600) of the culture solution after 48-hour culture was measured. The results are shown in Table 3.

Example 11: Preparation of Glucose Composition and Lactic Acid Fermentation Production The same procedure as in Example 10 was performed except that a glucose composition containing 100 g/L of glucose, 1.4 g/L of xylose (D(+)-xylose, manufactured by Wako Pure Chemical Industries, Ltd.), 0.2 g/L of acetic acid, 0.3 g/L of coumaric acid, and 0.014 g/L of ferulic acid was prepared. The results are shown in Table 3.

Example 12: Preparation of Glucose Composition and Lactic Acid Fermentation Production The same procedure as in Example 10 was performed except that a glucose composition containing 100 g/L of glucose, 22.3 g/L of xylose, 1 g/L of acetic acid, 0.5 g/L of coumaric acid, and 0.06 g/L of ferulic acid was prepared. The results are shown in Table 3.

Example 13: Preparation of Glucose Composition and Lactic Acid Fermentation Production The same procedure as in Example 10 was performed except that a glucose composition containing 100 g/L of glucose, 25 g/L of xylose, 4 g/L of acetic acid, 0.8 g/L of coumaric acid, and 0.14 g/L of ferulic acid was prepared. The results are shown in Table 3.

Comparative Example 9: Comparative Example of Glucose Composition in Lactic Acid Fermentation Production The same procedure as in Example 10 was performed except that a glucose composition containing only 100 g/L of glucose was prepared. The results are shown in Table 3.

Comparative Example 10: Comparative Example of Glucose Composition in Lactic Acid Fermentation The same procedure as in Example 10 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 3.

Comparative Example 11: Comparative Example of Glucose Composition in Lactic Acid Fermentation The same procedure as in Example 10 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 3.

Comparative Example 12: Comparative Example of Glucose Composition in Lactic Acid Fermentation The same procedure as in Example 10 was performed except that a glucose composition containing 100 g/L of glucose, 22.3 g/L of xylose, 1 g/L of acetic acid, 3 g/L of coumaric acid, and 0.06 g/L of ferulic acid was prepared. The results are shown in Table 3.

Comparative Example 13: Comparative Example of Glucose Composition in Lactic Acid Fermentation The same procedure as in Example 10 was performed except that a glucose composition containing 100 g/L of glucose, 22.3 g/L of xylose, 1 g/L of acetic acid, no coumaric acid, and 0.06 g/L of ferulic acid was prepared. The results are shown in Table 3.

Comparative Example 14: Comparative Example of Glucose Composition in Lactic Acid Fermentation The same procedure as in Example 10 was performed except that a glucose composition containing 100 g/L of glucose, 22.3 g/L of xylose, 1 g/L of acetic acid, 0.5 g/L of coumaric acid, and 0.4 g/L of ferulic acid was prepared. The results are shown in Table 3.

Comparative Example 15: Comparative Example of Glucose Composition in Lactic Acid Fermentation The same procedure as in Example 10 was performed except that a glucose composition containing 100 g/L of glucose, 22.3 g/L of xylose, 1 g/L of acetic acid, 0.5 g/L of coumaric acid, and no ferulic acid was prepared. The results are shown in Table 3.

Comparative Example 16: Comparative Example of Glucose Composition in Lactic Acid Fermentation The same procedure as in Example 10 was performed except that a glucose composition containing 100 g/L of glucose, 50 g/L of xylose, 1 g/L of acetic acid, 0.5 g/L of coumaric acid, and 0.06 g/L of ferulic acid was prepared. The results are shown in Table 3.

TABLE 3

Lactic acid fermentation test results using each glucose composition as fermentation raw material

| | Concentration in glucose composition (at the time of preparation) | | | | | Fermentation properties | | |
| --- | --- | --- | --- | --- | --- | --- | --- | --- |
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus theoretical ratio (%) |
| Example 10 | 100 | 0 | 0.2 | 0.3 | 0.014 | 3.4 | 0.36 | 88 |
| Example 11 | 100 | 1.4 | 0.2 | 0.3 | 0.014 | 3.5 | 0.35 | 88 |
| Example 12 | 100 | 22.3 | 1.0 | 0.5 | 0.06 | 3.3 | 0.38 | 91 |
| Example 13 | 100 | 25 | 4.0 | 0.8 | 0.14 | 3.4 | 0.40 | 90 |
| Comparative Example 9 | 100 | 0 | 0 | 0 | 0 | 2.5 | 0.25 | 82 |
| Comparative Example 10 | 100 | 22.3 | 15 | 0.5 | 0.06 | 2.4 | 0.20 | 83 |
| Comparative Example 11 | 100 | 22.3 | 0 | 0.5 | 0.06 | 2.5 | 0.25 | 80 |

TABLE 3-continued

Lactic acid fermentation test results using each glucose composition as fermentation raw material

|  | Concentration in glucose composition (at the time of preparation) | | | | | Fermentation properties | | |
| --- | --- | --- | --- | --- | --- | --- | --- | --- |
|  | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus theoretical ratio (%) |
| Comparative Example 12 | 100 | 22.3 | 1.0 | 3.0 | 0.06 | 2.2 | 0.18 | 77 |
| Comparative Example 13 | 100 | 22.3 | 1.0 | 0 | 0.06 | 2.5 | 0.23 | 83 |
| Comparative Example 14 | 100 | 22.3 | 1.0 | 0.5 | 0.4 | 2.4 | 0.22 | 82 |
| Comparative Example 15 | 100 | 22.3 | 1.0 | 0.5 | 0 | 2.6 | 0.25 | 81 |
| Comparative Example 16 | 100 | 50 | 1.0 | 0.5 | 0.06 | 2.6 | 0.25 | 83 |

Example 14: Preparation of Glucose Composition Using Cellulose-Containing Biomass as Raw Material and Lactic Acid Fermentation Production By using the glucose composition prepared in Example 5, lactic acid fermentation was performed in the same manner as in Example 10. The results are shown in Table 4.

Example 15: Preparation of Glucose Composition Using Cellulose-Containing Biomass as Raw Material and Lactic Acid Fermentation Production By using the glucose composition prepared in Example 6, lactic acid fermentation was performed in the same manner as in Example 10. The results are shown in Table 4.

Example 16: Preparation of Glucose Composition Using Cellulose-Containing Biomass as Raw Material and Lactic Acid Fermentation Production By using the glucose composition prepared in Example 7, lactic acid fermentation was performed in the same manner as in Example 10. The results are shown in Table 4.

Example 17: Preparation of Glucose Composition Using Cellulose-Containing Biomass as Raw Material and Lactic Acid Fermentation Production By using the glucose composition prepared in Example 8, lactic acid fermentation was performed in the same manner as in Example 10. The results are shown in Table 4.

Example 18: Preparation of Glucose Composition Using Cellulose-Containing Biomass as Raw Material and Lactic Acid Fermentation Production By using the glucose composition prepared in Example 9, lactic acid fermentation was performed in the same manner as in Example 10. The results are shown in Table 4.

TABLE 4

Lactic acid fermentation test results using each glucose composition as fermentation raw material

|  | Concentration in glucose composition (at the time of preparation) | | | | | | Fermentation properties | | |
| --- | --- | --- | --- | --- | --- | --- | --- | --- | --- |
|  | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus theoretical ratio (%) |
| Example 14 | 100 | 11.1 | 1.0 | 0.5 | 0.06 | 128 | 3.8 | 0.53 | 98 |
| Example 15 | 100 | 11.1 | 1.0 | 0.5 | 0.06 | 12 | 3.4 | 0.39 | 91 |
| Example 16 | 100 | 11.1 | 1.0 | 0.5 | 0.06 | 20 | 3.7 | 0.51 | 98 |
| Example 17 | 100 | 11.1 | 1.0 | 0.5 | 0.06 | 350 | 3.9 | 0.49 | 98 |
| Example 18 | 100 | 11.1 | 1.0 | 0.5 | 0.06 | 1040 | 3.0 | 0.35 | 90 |
| Comparative Example 19 | 100 | 0 | 0 | 0 | 0 | 0 | 2.5 | 0.25 | 82 |

Reference Example 7: Preparation of Succinic Acid Fermentation Bacterium to be Used in Succinic Acid Fermentation Evaluation Test As a succinic acid fermentation microorganism, *Actinobacillus Succinogenes* (*Actinobacillus Succinogenes*) ATCC 55618 strain was used. 2 mL of a culture medium composed of Triptic Soy Broth (manufactured by Wako Pure Chemical Industries, Ltd.) was placed in each of five test tubes in total, and in a clean bench, 0.2 mL of a glycerol stock of *Actinobacillus Succinogenes* was inoculated therein. This was subjected to reciprocal shaking culture with an inclination of 50° at 37° C. and 120 rpm for 24 hours using a shaker (BIO-SHAKER BR-40LF, manufactured by TAITEC CORPORATION), whereby a total of 10 mL of a preculture solution was obtained. The preculture solution was centrifuged at 15,000×g for 5 minutes at 4° C., and the supernatant was removed and, thereafter, the residue was suspended in 1 mL of a saline solution, whereby a precultured bacterial cell solution with an OD of 8.0 was obtained.

Example 19: Preparation of Glucose Composition and Succinic Acid Fermentation Production A glucose composition was prepared by dissolving glucose (D(+)-glucose, manufactured by Wako Pure Chemical Industries, Ltd.) at 100 g/L, acetic acid (reagent special grade, 99.7%, manufactured by Wako Pure Chemical Industries, Ltd.) at 0.2 g/L, coumaric acid (trans-p-coumaric acid, manufactured by Tokyo Chemical Industry Co., Ltd.) at 0.3 g/L, and ferulic acid (trans-ferulic acid, manufactured by Tokyo Chemical Industry Co., Ltd.) at 0.014 g/L in pure water. Coumaric acid and ferulic acid are not dissolved under acidic conditions and, therefore, a 1 g/L concentrate of each component with a pH of 8 was prepared using a 6 N aqueous sodium hydroxide solution, and the glucose composition was prepared by diluting the concentrates. Further, the glucose composition was adjusted to a final pH of 7 using 6 N sodium hydroxide.

To 4.5 mL of the prepared glucose composition, 5.5 mL of a concentrate obtained by dissolving the following components as auxiliary raw materials such as a nitrogen source at final concentrations as indicated: Bacto™ Yeast Extract (manufactured by Nippon Becton Dickinson Company, Ltd.) at 16 g/L, corn steep liquor (CSL) (manufactured by Oji Cornstarch Co., Ltd.) at 12 g/L, potassium dihydrogen phosphate at 3 g/L, dipotassium hydrogen phosphate at 1.5 g/L, sodium chloride at 1 g/L, magnesium chloride hexahydrate at 0.64 g/L, calcium chloride at 0.3 g/L, and magnesium carbonate at 40 g/L was added, and 0.2 mL of the preculture solution described in Reference Example 7 was inoculated therein. This was subjected to static culture at 37° C. for 144 hours. Sampling was performed about every 24 hours, and the sugar concentration and the succinic acid concentration were analyzed by the methods described in Reference Examples 2 and 6, and the maximum fermentation rate and the fermentation yield versus the theoretical ratio (the theoretical ratio when the theoretical yield of succinic acid was assumed to be 0.66 g/g—the total consumed sugar) were determined. As the evaluation of microbial growth potential, the OD (OD600) of the culture solution after 48-hour culture was measured. The results are shown in Table 5.

Example 20: Preparation of Glucose Composition and Succinic Acid Fermentation Production The same procedure as in Example 19 was performed except that a glucose composition containing 100 g/L of glucose, 1.4 g/L of xylose, 0.2 g/L of acetic acid, 0.3 g/L of coumaric acid, and 0.014 g/L of ferulic acid was prepared. The results are shown in Table 5.

Example 21: Preparation of Glucose Composition and Succinic Acid Fermentation Production The same procedure as in Example 19 was performed except that a glucose composition containing 100 g/L of glucose, 22.3 g/L of xylose, 1.0 g/L of acetic acid, 0.5 g/L of coumaric acid, and 0.06 g/L of ferulic acid was prepared. The results are shown in Table 5.

Example 22: Preparation of Glucose Composition and Succinic Acid Fermentation Production The same procedure as in Example 19 was performed except that a glucose composition containing 100 g/L of glucose, 25.0 g/L of xylose, 4 g/L of acetic acid, 0.8 g/L of coumaric acid, and 0.14 g/L of ferulic acid was prepared. The results are shown in Table 5.

Comparative Example 17: Comparative Example of Glucose Composition in Succinic Acid Fermentation Production The same procedure as in Example 19 was performed except that a glucose composition containing only 100 g/L of glucose was prepared. The results are shown in Table 5.

Comparative Example 18: Comparative Example of Glucose Composition in Succinic Acid Fermentation Production The same procedure as in Example 19 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 5.

Comparative Example 19: Comparative Example of Glucose Composition in Succinic Acid Fermentation Production The same procedure as in Example 19 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 5.

Comparative Example 20: Comparative Example of Glucose Composition in Succinic Acid Fermentation Production The same procedure as in Example 19 was performed except that a glucose composition containing 100 g/L of glucose, 22.3 g/L of xylose, 1.0 g/L of acetic acid, 3.0 g/L of coumaric acid, and 0.06 g/L of ferulic acid was prepared. The results are shown in Table 5.

Comparative Example 21: Comparative Example of Glucose Composition in Succinic Acid Fermentation Production The same procedure as in Example 19 was performed except that a glucose composition containing 100 g/L of glucose, 22.3 g/L of xylose, 1.0 g/L of acetic acid, no coumaric acid, and 0.06 g/L of ferulic acid was prepared. The results are shown in Table 5.

Comparative Example 22: Comparative Example of Glucose Composition in Succinic Acid Fermentation Production The same procedure as in Example 19 was performed except that a glucose composition containing 100 g/L of glucose, 22.3 g/L of xylose, 1.0 g/L of acetic acid, 0.5 g/L of coumaric acid, and 0.4 g/L of ferulic acid was prepared. The results are shown in Table 5.

Comparative Example 23: Comparative Example of Glucose Composition in Succinic Acid Fermentation Production The same procedure as in Example 19 was performed except that a glucose composition containing 100 g/L of glucose, 22.3 g/L of xylose, 1.0 g/L of acetic acid, 0.5 g/L of coumaric acid, and no ferulic acid was prepared. The results are shown in Table 5.

Comparative Example 24: Comparative Example of Glucose Composition in Succinic Acid Fermentation Production The same procedure as in Example 19 was performed except that a glucose composition containing 100 g/L of glucose, 50 g/L of xylose, 1.0 g/L of acetic acid, 0.5 g/L of coumaric acid, and 0.06 g/L of ferulic acid was prepared. The results are shown in Table 5.

Example 23: Preparation of Glucose Composition Using Cellulose-Containing Biomass as Raw Material and Succinic Acid Fermentation Production By using the glucose composition shown in Example 5, succinic acid fermentation was performed in the same manner as in Example 19. The results are shown in Table 6.

Example 24: Preparation of Glucose Composition Using Cellulose-Containing Biomass as Raw Material and Succinic Acid Production By using the glucose composition shown in Example 6, succinic acid fermentation was performed in the same manner as in Example 19. The results are shown in Table 6.

Example 25: Preparation of Glucose Composition Using Cellulose-Containing Biomass as Raw Material and Succinic Acid Production By using the glucose composition shown in Example 7, succinic acid fermentation was performed in the same manner as in Example 19. The results are shown in Table 6.

Example 26: Preparation of Glucose Composition Using Cellulose-Containing Biomass as Raw Material and Succinic Acid Production By using the glucose composition shown in Example 8, succinic acid fermentation was performed in the same manner as in Example 19. The results are shown in Table 6.

TABLE 5

Succinic acid fermentation test results using each glucose composition as fermentation raw material

| | Concentration in glucose composition (at the time of preparation) | | | | | Fermentation properties | | |
| --- | --- | --- | --- | --- | --- | --- | --- | --- |
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus theoretical ratio (%) |
| Example 19 | 100 | 0 | 0.2 | 0.3 | 0.014 | 5.4 | 0.49 | 90 |
| Example 20 | 100 | 1.4 | 0.2 | 0.3 | 0.014 | 5.4 | 0.48 | 90 |
| Example 21 | 100 | 22.3 | 1.0 | 0.5 | 0.06 | 5.8 | 0.50 | 91 |
| Example 22 | 100 | 25.0 | 4.0 | 0.8 | 0.14 | 5.8 | 0.52 | 92 |
| Comparative Example 17 | 100 | 0 | 0 | 0 | 0 | 4.8 | 0.42 | 85 |
| Comparative Example 18 | 100 | 22.3 | 15 | 0.5 | 0.06 | 4.0 | 0.40 | 82 |
| Comparative Example 19 | 100 | 22.3 | 0 | 0.5 | 0.06 | 4.8 | 0.35 | 78 |
| Comparative Example 20 | 100 | 22.3 | 1.0 | 3.0 | 0.06 | 3.6 | 0.28 | 70 |
| Comparative Example 21 | 100 | 22.3 | 1.0 | 0 | 0.06 | 4.6 | 0.36 | 83 |
| Comparative Example 22 | 100 | 22.3 | 1.0 | 0.5 | 0.4 | 4.0 | 0.34 | 78 |
| Comparative Example 23 | 100 | 22.3 | 1.0 | 0.5 | 0 | 4.8 | 0.38 | 84 |
| Comparative Example 24 | 100 | 50 | 1.0 | 0.5 | 0.06 | 4.8 | 0.42 | 85 |

Example 27: Preparation of Glucose Composition Using Cellulose-Containing Biomass as Raw Material and Succinic Acid Production By using the glucose composition shown in Example 9, succinic acid fermentation was performed in the same manner as in Example 19. The results are shown in Table 6.

mixed, and the resulting mixture was incubated at a temperature of 37° C. for 1 hour. After 50 µL of the resulting reaction solution was dissolved in 1 mL of acetonitrile, the resulting mixture was centrifuged at 10,000 rpm for 5 minutes, and thereafter, 10 µL of the supernatant was analyzed by HPLC.

Detection method: UV 360 nm.

TABLE 6

Succinic acid fermentation test results using each glucose composition as fermentation raw material

| | Concentration in glucose composition (at the time of preparation) | | | | | | Fermentation properties | | |
|---|---|---|---|---|---|---|---|---|---|
| | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus theoretical ratio (%) |
| Example 23 | 100 | 22.3 | 1.0 | 0.5 | 0.06 | 128 | 6.5 | 0.58 | 99 |
| Example 24 | 100 | 22.3 | 1.0 | 0.5 | 0.06 | 12 | 5.8 | 0.49 | 91 |
| Example 25 | 100 | 22.3 | 1.0 | 0.5 | 0.06 | 20 | 6.2 | 0.57 | 98 |
| Example 26 | 100 | 22.3 | 1.0 | 0.5 | 0.06 | 350 | 6.5 | 0.58 | 98 |
| Example 27 | 100 | 22.3 | 1.0 | 0.5 | 0.06 | 1040 | 5.6 | 0.47 | 89 |
| Comparative Example 17 | 100 | 0 | 0 | 0 | 0 | 0 | 4.8 | 0.42 | 85 |

Reference Example 8: Preparation of Cadaverine Fermentation Bacterium to be Used in Amino Acid Fermentation Evaluation Test As a microorganism which produces cadaverine, *Corynebacterium glutamicum* (*Corynebacterium gulutamicum*) TR-CAD1 strain described in JP-A-2004-222569 was used, and cadaverine fermentation, in which glucose is assimilated, was examined.

The TR-CAD1 strain was inoculated in a test tube along with 100 mL of a culture medium containing 45 g/L of glucose, 1 g/L of citric acid, 15 g/L of urea, 0.5 g/L of potassium dihydrogen phosphate, 0.5 g/L of dipotassium hydrogen phosphate, 0.5 g/L of magnesium sulfate, 0.8 g/L of L-threonine, 0.6 g/L of L-methionine, 1.5 g/L of L-leucine, 6 mg/L of iron sulfate heptahydrate, 4.2 g/L of manganese sulfate monohydrate, 1 mg/L of biotin, 2 mg/L of thiamine, and 25 µg/mL of kanamycin, and subjected to shaking culture overnight (preculture). The *Corynebacterium glutamicum* TR-CAD1 strain was collected from the preculture solution by centrifugation and washed well with 15 mL of sterilized water, whereby a preculture solution with an OD of 5 was obtained.

Reference Example 9: Measurement of Lysine and Cadaverine Concentrations

The concentrations of lysine and cadaverine contained in the sugar solution were quantitatively determined under the following HPLC conditions compared to a reference standard:

Column: CAPCELL PAK C18 (manufactured by Shiseido Company, Limited)

Mobile phase: (a 0.1% aqueous phosphoric acid solution: acetonitrile)=(4.5:5.5)

Sample pretreatment: To 25 µL of an analysis sample, as an internal standard, 25 µL of 1,4-diaminobutane (0.03 M), 150 µL of sodium hydrogen carbonate (0.075 M) and an ethanol solution of 2,4-dinitrofluorobenzene (0.2 M) were added and

Example 28: Preparation of Glucose Composition and Cadaverine Fermentation Production A glucose composition was prepared by dissolving glucose (D(+)-glucose, manufactured by Wako Pure Chemical Industries, Ltd.) at 100 g/L, acetic acid (reagent special grade, 99.7%, manufactured by Wako Pure Chemical Industries, Ltd.) at 0.2 g/L, coumaric acid (trans-p-coumaric acid, manufactured by Tokyo Chemical Industry Co., Ltd.) at 0.3 g/L, and ferulic acid (trans-ferulic acid, manufactured by Tokyo Chemical Industry Co., Ltd.) at 0.014 g/L in pure water. Coumaric acid and ferulic acid are not dissolved under acidic conditions and, therefore, a 1 g/L concentrate of each component with a pH of 8 was prepared using a 6 N aqueous sodium hydroxide solution, and the glucose composition was prepared by diluting the concentrates. Further, the glucose composition was adjusted to a final pH of 7 using 6 N sodium hydroxide.

To 4.5 mL of the prepared glucose composition, 5.5 mL of a concentrate obtained by dissolving the following components as auxiliary raw materials at final concentrations as indicated: citric acid at 1 g/L, urea at 15 g/L, potassium dihydrogen phosphate at 0.5 g/L, dipotassium hydrogen phosphate at 0.5 g/L, magnesium sulfate at 0.5 g/L, L-threonine at 0.8 g/L, L-methionine at 0.6 g/L, L-leucine at 1.5 g/L, iron sulfate heptahydrate at 6 mg/L, manganese sulfate monohydrate at 4.2 g/L, biotin at 1 mg/L, and thiamine at 2 mg/L was added, and 0.2 mL of the preculture solution described in Reference Example 8 was inoculated therein. This was subjected to shaking culture at 37° C. for 48 hours. Sampling was performed about every 12 hours, and the sugar concentration and the cadaverine concentration were analyzed by the methods described in Reference Examples 2 and 9, and the maximum fermentation rate and the fermentation yield versus the consumed glucose ratio were determined. As the evaluation of microbial growth potential, the OD (OD600) of the culture solution after 48-hour culture was measured. The results are shown in Table 7.

Example 29: Preparation of Glucose Composition and Cadaverine Fermentation Production The same procedure as in Example 28 was performed except that a glucose composition containing 100 g/L of glucose, 1.4 g/L of xylose, 0.2 g/L of acetic acid, 0.3 g/L of coumaric acid, and 0.014 g/L of ferulic acid was prepared. The results are shown in Table 7.

Example 30: Preparation of Glucose Composition and Cadaverine Fermentation Production The same procedure as in Example 28 was performed except that a glucose composition containing 100 g/L of glucose, 22.3 g/L of xylose, 1.0 g/L of acetic acid, 0.5 g/L of coumaric acid, and 0.06 g/L of ferulic acid was prepared. The results are shown in Table 7.

Example 31: Preparation of Glucose Composition and Cadaverine Fermentation Production The same procedure as in Example 28 was performed except that a glucose composition containing 100 g/L of glucose, 25.0 g/L of xylose, 4 g/L of acetic acid, 0.8 g/L of coumaric acid, and 0.14 g/L of ferulic acid was prepared. The results are shown in Table 7.

Comparative Example 25: Comparative Example of Glucose Composition in Cadaverine Fermentation Production The same procedure as in Example 28 was performed except that a glucose composition containing only 100 g/L of glucose was prepared. The results are shown in Table 7.

Comparative Example 26: Comparative Example of Glucose Composition in Cadaverine Fermentation Production The same procedure as in Example 28 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 7.

Comparative Example 27: Comparative Example of Glucose Composition in Cadaverine Fermentation Production The same procedure as in Example 28 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 7.

Comparative Example 28: Comparative Example of Glucose Composition in Cadaverine Fermentation Production The same procedure as in Example 28 was performed except that a glucose composition containing 100 g/L of glucose, 22.3 g/L of xylose, 1.0 g/L of acetic acid, 3.0 g/L of coumaric acid, and 0.06 g/L of ferulic acid was prepared. The results are shown in Table 7.

Comparative Example 29: Comparative Example of Glucose Composition in Cadaverine Fermentation Production The same procedure as in Example 28 was performed except that a glucose composition containing 100 g/L of glucose, 22.3 g/L of xylose, 1.0 g/L of acetic acid, no coumaric acid, and 0.06 g/L of ferulic acid was prepared. The results are shown in Table 7.

Comparative Example 30: Comparative Example of Glucose Composition in Cadaverine Fermentation Production The same procedure as in Example 28 was performed except that a glucose composition containing 100 g/L of glucose, 22.3 g/L of xylose, 1.0 g/L of acetic acid, 0.5 g/L of coumaric acid, and 0.4 g/L of ferulic acid was prepared. The results are shown in Table 7.

Comparative Example 31: Comparative Example of Glucose Composition in Cadaverine Fermentation Production The same procedure as in Example 28 was performed except that a glucose composition containing 100 g/L of glucose, 22.3 g/L of xylose, 1.0 g/L of acetic acid, 0.5 g/L of coumaric acid, and no ferulic acid was prepared. The results are shown in Table 7.

Comparative Example 32: Comparative Example of Glucose Composition in Cadaverine Fermentation Production The same procedure as in Example 28 was performed except that a glucose composition containing 100 g/L of glucose, 50 g/L of xylose, 1.0 g/L of acetic acid, 0.5 g/L of coumaric acid, and 0.06 g/L of ferulic acid was prepared. The results are shown in Table 7.

TABLE 7

Cadaverine fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus consumed glucose ratio (%) |
| Example 28 | 100 | 0 | 0.2 | 0.3 | 0.014 | 4.8 | 0.07 | 7.8 |
| Example 29 | 100 | 1.4 | 0.2 | 0.3 | 0.014 | 5.0 | 0.07 | 7.7 |
| Example 30 | 100 | 22.3 | 1.0 | 0.5 | 0.06 | 5.5 | 0.07 | 7.9 |

TABLE 7-continued

Cadaverine fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus consumed glucose ratio (%) |
| Example 31 | 100 | 25.0 | 4.0 | 0.8 | 0.14 | 5.2 | 0.07 | 7.8 |
| Comparative Example 25 | 100 | 0 | 0 | 0 | 0 | 3.5 | 0.04 | 4.5 |
| Comparative Example 26 | 100 | 22.3 | 15 | 0.5 | 0.06 | 2.9 | 0.05 | 5.2 |
| Comparative Example 27 | 100 | 22.3 | 0 | 0.5 | 0.06 | 3.0 | 0.04 | 4.7 |
| Comparative Example 28 | 100 | 22.3 | 1.0 | 3.0 | 0.06 | 2.8 | 0.05 | 5.5 |
| Comparative Example 29 | 100 | 22.3 | 1.0 | 0 | 0.06 | 3.0 | 0.05 | 5.0 |
| Comparative Example 30 | 100 | 22.3 | 1.0 | 0.5 | 0.4 | 2.7 | 0.04 | 4.6 |
| Comparative Example 31 | 100 | 22.3 | 1.0 | 0.5 | 0 | 2.9 | 0.05 | 4.8 |
| Comparative Example 32 | 100 | 50 | 1.0 | 0.5 | 0.06 | 4.2 | 0.05 | 6.0 |

Example 32: Preparation of Glucose Composition Using Cellulose-Containing Biomass as Raw Material and Cadaverine Fermentation Production By using the glucose composition shown in Example 5, cadaverine fermentation was performed in the same manner as in Example 28. The results are shown in Table 8.

Example 33: Preparation of Glucose Composition Using Cellulose-Containing Biomass as Raw Material and Cadaverine Fermentation Production By using the glucose composition shown in Example 6, cadaverine fermentation was performed in the same manner as in Example 28. The results are shown in Table 8.

Example 34: Preparation of Glucose Composition Using Cellulose-Containing Biomass as Raw Material and Cadaverine Fermentation Production By using the glucose composition shown in Example 7, cadaverine fermentation was performed in the same manner as in Example 28. The results are shown in Table 8.

Example 35: Preparation of Glucose Composition Using Cellulose-Containing Biomass as Raw Material and Cadaverine Fermentation Production By using the glucose composition shown in Example 8, cadaverine fermentation was performed in the same manner as in Example 28. The results are shown in Table 8.

Example 36: Preparation of Glucose Composition Using Cellulose-Containing Biomass as Raw Material and Cadaverine Fermentation Production By using the glucose composition shown in Example 9, cadaverine fermentation was performed in the same manner as in Example 28. The results are shown in Table 8.

TABLE 8

Cadaverine fermentation test results using each glucose composition as fermentation raw material

| | Concentration in glucose composition (at the time of preparation) | | | | | | Fermentation properties | | |
|---|---|---|---|---|---|---|---|---|---|
| | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus consumed glucose ratio (%) |
| Example 32 | 100 | 22.3 | 1.0 | 0.5 | 0.06 | 128 | 5.5 | 0.08 | 9.0 |
| Example 33 | 100 | 22.3 | 1.0 | 0.5 | 0.06 | 12 | 5.4 | 0.08 | 8.7 |
| Example 34 | 100 | 22.3 | 1.0 | 0.5 | 0.06 | 20 | 5.4 | 0.08 | 8.7 |
| Example 35 | 100 | 22.3 | 1.0 | 0.5 | 0.06 | 350 | 5.5 | 0.08 | 8.9 |
| Example 36 | 100 | 22.3 | 1.0 | 0.5 | 0.06 | 1040 | 5.5 | 0.07 | 8.0 |
| Comparative Example 25 | 100 | 0 | 0 | 0 | 0 | 0 | 3.5 | 0.04 | 4.5 |

Reference Example 10: Preparation of Lysine Fermentation Bacterium to be Used in Amino Acid Fermentation Evaluation Test To produce *Corynebacterium glutamicum* that can synthesize lysine, a lysine-producing bacterium was produced by introducing an effective mutation into a lysine biosynthesis gene. *Corynebacterium glutamicum* AK-1 strain (hereinafter abbreviated as "AK-1 strain") was produced according to the method described in Apppl. Microbiol. Biotechnol., (2002), 58, p. 217-223. In this strain, feedback inhibition by lysine and threonine is canceled. Therefore, lysine can be synthesized by culture. By using the AK-1 strain, lysine fermentation, in which glucose is assimilated, was examined.

The AK-1 strain was inoculated in a test tube along with 100 mL of a culture medium containing 45 g/L of glucose, 1 g/L of citric acid, 15 g/L of urea, 0.5 g/L of potassium dihydrogen phosphate, 0.5 g/L of dipotassium hydrogen phosphate, 0.5 g/L of magnesium sulfate, 0.8 g/L of L-threonine, 0.6 g/L of L-methionine, 1.5 g/L of L-leucine, 6 mg/L of iron sulfate heptahydrate, 4.2 g/L of manganese sulfate monohydrate, 1 mg/L of biotin, 2 mg/L of thiamine, and 25 µg/mL of kanamycin, and subjected to shaking culture overnight (preculture). The AK-1 strain was collected from the preculture solution by centrifugation and washed well with 15 mL of sterilized water, whereby a preculture solution with an OD of 5 was obtained.

Example 37: Preparation of Glucose Composition and Lysine Fermentation Production A glucose composition was prepared by dissolving glucose (D(+)-glucose, manufactured by Wako Pure Chemical Industries, Ltd.) at 100 g/L, acetic acid (reagent special grade, 99.7%, manufactured by Wako Pure Chemical Industries, Ltd.) at 0.2 g/L, coumaric acid (trans-p-coumaric acid, manufactured by Tokyo Chemical Industry Co., Ltd.) at 0.3 g/L, and ferulic acid (trans-ferulic acid, manufactured by Tokyo Chemical Industry Co., Ltd.) at 0.014 g/L in pure water. Coumaric acid and ferulic acid are not dissolved under acidic conditions, and therefore, a 1 g/L concentrate of each component with a pH of 8 was prepared using a 6 N aqueous sodium hydroxide solution, and the glucose composition was prepared by diluting the concentrates. Further, the glucose composition was adjusted to a final pH of 7 using 6 N sodium hydroxide.

To 4.5 mL of the prepared glucose composition, 5.5 mL of a concentrate obtained by dissolving the following components as auxiliary raw materials at final concentrations as indicated: citric acid at 1 g/L, urea at 15 g/L, potassium dihydrogen phosphate at 0.5 g/L, dipotassium hydrogen phosphate at 0.5 g/L, magnesium sulfate at 0.5 g/L, L-threonine at 0.8 g/L, L-methionine at 0.6 g/L, L-leucine at 1.5 g/L, iron sulfate heptahydrate at 6 mg/L, manganese sulfate monohydrate at 4.2 g/L, biotin at 1 mg/L, and thiamine at 2 mg/L was added, and 0.2 mL of the preculture solution described in Reference Example 10 was inoculated therein. This was subjected to shaking culture at 37° C. for 48 hours. Sampling was performed about every 12 hours, and the sugar concentration and the lysine concentration were analyzed by the methods described in Reference Examples 2 and 9, and the maximum fermentation rate and the fermentation yield versus the consumed glucose ratio were determined. As the evaluation of microbial growth potential, the OD (OD600) of the culture solution after 48-hour culture was measured. The results are shown in Table 9.

Example 38: Preparation of Glucose Composition and Lysine Fermentation Production The same procedure as in Example 37 was performed except that a glucose composition containing 100 g/L of glucose, 1.4 g/L of xylose, 0.2 g/L of acetic acid, 0.3 g/L of coumaric acid, and 0.014 g/L of ferulic acid was prepared. The results are shown in Table 9.

Example 39: Preparation of Glucose Composition and Lysine Fermentation Production The same procedure as in Example 37 was performed except that a glucose composition containing 100 g/L of glucose, 22.3 g/L of xylose, 1.0 g/L of acetic acid, 0.5 g/L of coumaric acid, and 0.06 g/L of ferulic acid was prepared. The results are shown in Table 9.

Example 40: Preparation of Glucose Composition and Lysine Fermentation Production The same procedure as in Example 37 was performed except that a glucose composition containing 100 g/L of glucose, 25.0 g/L of xylose, 4 g/L of acetic acid, 0.8 g/L of coumaric acid, and 0.14 g/L of ferulic acid was prepared. The results are shown in Table 9.

Comparative Example 33: Comparative Example of Glucose Composition in Lysine Fermentation Production The same procedure as in Example 37 was performed except that a glucose composition containing only 100 g/L of glucose was prepared. The results are shown in Table 9.

Comparative Example 34: Comparative Example of Glucose Composition in Lysine Fermentation Production The same procedure as in Example 37 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 9.

Comparative Example 35: Comparative Example of Glucose Composition in Lysine Fermentation Production The same procedure as in Example 37 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 9.

Comparative Example 36: Comparative Example of Glucose Composition in Lysine Fermentation Production The same procedure as in Example 37 was performed except that a glucose composition containing 100 g/L of glucose, 22.3 g/L of xylose, 1.0 g/L of acetic acid, 3.0 g/L of coumaric acid, and 0.06 g/L of ferulic acid was prepared. The results are shown in Table 9.

Comparative Example 37: Comparative Example of Glucose Composition in Lysine Fermentation Production The same procedure as in Example 37 was performed except that a glucose composition containing 100 g/L of glucose, 22.3 g/L of xylose, 1.0 g/L of acetic acid, no coumaric acid, and 0.06 g/L of ferulic acid was prepared. The results are shown in Table 9.

Comparative Example 38: Comparative Example of Glucose Composition in Lysine Fermentation Production The same procedure as in Example 37 was performed except that a glucose composition containing 100 g/L of glucose, 22.3 g/L of xylose, 1.0 g/L of acetic acid, 0.5 g/L of coumaric acid, and 0.4 g/L of ferulic acid was prepared. The results are shown in Table 9.

Comparative Example 39: Comparative Example of Glucose Composition in Lysine Fermentation Production The same procedure as in Example 37 was performed except that a glucose composition containing 100 g/L of glucose, 22.3 g/L of xylose, 1.0 g/L of acetic acid, 0.5 g/L of coumaric acid, and no ferulic acid was prepared. The results are shown in Table 9.

Comparative Example 40: Comparative Example of Glucose Composition in Lysine Fermentation Production The same procedure as in Example 37 was performed except that a glucose composition containing 100 g/L of glucose, 50 g/L of xylose, 1.0 g/L of acetic acid, 0.5 g/L of coumaric acid, and 0.06 g/L of ferulic acid was prepared. The results are shown in Table 9.

Example 41: Preparation of Glucose Composition Using Cellulose-Containing Biomass as Raw Material and Lysine Fermentation Production By using the glucose composition shown in Example 5, lysine fermentation was performed in the same manner as in Example 37. The results are shown in Table 10.

Example 42: Preparation of Glucose Composition Using Cellulose-Containing Biomass as Raw Material and Lysine Fermentation Production By using the glucose composition shown in Example 6, lysine fermentation was performed in the same manner as in Example 37. The results are shown in Table 10.

Example 43: Preparation of Glucose Composition Using Cellulose-Containing Biomass as Raw Material and Lysine Fermentation Production By using the glucose composition shown in Example 7, lysine fermentation was performed in the same manner as in Example 37. The results are shown in Table 10.

Example 44: Preparation of Glucose Composition Using Cellulose-Containing Biomass as Raw Material and Lysine Fermentation Production By using the glucose composition shown in Example 8, lysine fermentation was performed in the same manner as in Example 37. The results are shown in Table 10.

Example 45: Preparation of Glucose Composition Using Cellulose-Containing Biomass as Raw Material and Lysine Fermentation Production By using the glucose composition shown in Example 9, lysine fermentation was performed in the same manner as in Example 37. The results are shown in Table 10.

TABLE 9

Lysine fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus consumed glucose ratio (%) |
| Example 37 | 100 | 0 | 0.2 | 0.3 | 0.014 | 10.5 | 0.3 | 33 |
| Example 38 | 100 | 1.4 | 0.2 | 0.3 | 0.014 | 11.0 | 0.3 | 33 |
| Example 39 | 100 | 22.3 | 1.0 | 0.5 | 0.06 | 12.0 | 0.4 | 38 |
| Example 40 | 100 | 25.0 | 4.0 | 0.8 | 0.14 | 10.8 | 0.3 | 35 |
| Comparative Example 33 | 100 | 0 | 0 | 0 | 0 | 8.1 | 0.2 | 24 |
| Comparative Example 34 | 100 | 22.3 | 15 | 0.5 | 0.06 | 7.2 | 0.2 | 20 |
| Comparative Example 35 | 100 | 22.3 | 0 | 0.5 | 0.06 | 8.1 | 0.2 | 23 |
| Comparative Example 36 | 100 | 22.3 | 1.0 | 3.0 | 0.06 | 7.5 | 0.2 | 18 |
| Comparative Example 37 | 100 | 22.3 | 1.0 | 0 | 0.06 | 8.1 | 0.2 | 22 |
| Comparative Example 38 | 100 | 22.3 | 1.0 | 0.5 | 0.4 | 7.2 | 0.2 | 18 |
| Comparative Example 39 | 100 | 22.3 | 1.0 | 0.5 | 0 | 8.0 | 0.2 | 20 |
| Comparative Example 40 | 100 | 50 | 1.0 | 0.5 | 0.06 | 9.8 | 0.2 | 25 |

TABLE 10

Lysine fermentation test results using each glucose composition as fermentation raw material

| | Concentration in glucose composition (at the time of preparation) | | | | | | Fermentation properties | | |
|---|---|---|---|---|---|---|---|---|---|
| | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus consumed glucose ratio (%) |
| Example 41 | 100 | 22.3 | 1.0 | 0.5 | 0.06 | 128 | 11.0 | 0.4 | 40 |
| Example 42 | 100 | 22.3 | 1.0 | 0.5 | 0.06 | 12 | 10.5 | 0.3 | 37 |
| Example 43 | 100 | 22.3 | 1.0 | 0.5 | 0.06 | 20 | 10.7 | 0.4 | 38 |
| Example 44 | 100 | 22.3 | 1.0 | 0.5 | 0.06 | 350 | 11.2 | 0.4 | 40 |
| Example 45 | 100 | 22.3 | 1.0 | 0.5 | 0.06 | 1040 | 12.0 | 0.3 | 35 |
| Comparative Example 33 | 100 | 0 | 0 | 0 | 0 | 0 | 8.1 | 0.2 | 24 |

Reference Example 11: Preparation of Yeast (*Shizosaccharomyces pombe*) to be Used in Ethanol Fermentation Evaluation Test As an ethanol fermentation microorganism, *Shizosaccharomyces pombe* (*Shizosaccharomyces pombe*) NBRC 1628 strain was used. 2 mL of YPD medium (which was prepared to contain 20 g/L of peptone, 10 g/L of yeast extract, and 10 g/L of glucose after separately sterilizing peptone, a yeast extract concentrate, and a glucose concentrate by autoclaving at 121° C. for 20 minutes) was placed in a test tube, and in a clean bench, a colony of the yeast formed by plate culture (30° C., 1 to 2 days) on YPD agar medium was inoculated therein using a platinum loop. This was subjected to reciprocal shaking culture with an inclination of 50° at 30° C. and 120 rpm for 24 hours using a shaker (BIO-SHAKER BR40LF, manufactured by TAITEC CORPORATION), whereby a preculture solution was obtained. The preculture solution was centrifuged at 15,000×g for 5 minutes at 4° C., and the supernatant was removed and, thereafter, the residue was suspended in 2 mL of a saline solution, whereby a precultured bacterial cell solution with an OD of 7.5 was obtained.

Example 46: Preparation of Glucose Composition and Ethanol Fermentation Production A glucose composition was prepared by dissolving glucose (D(+)-glucose, manufactured by Wako Pure Chemical Industries, Ltd.) at 100 g/L, acetic acid (reagent special grade, 99.7%, manufactured by Wako Pure Chemical Industries, Ltd.) at 0.1 g/L, coumaric acid (trans-p-coumaric acid, manufactured by Tokyo Chemical Industry Co., Ltd.) at 0.15 g/L, and ferulic acid (trans-ferulic acid, manufactured by Tokyo Chemical Industry Co., Ltd.) at 0.007 g/L in pure water. Coumaric acid and ferulic acid are not dissolved under acidic conditions and, therefore, a 1 g/L concentrate of each component with a pH of 8 was prepared using a 6 N aqueous sodium hydroxide solution, and the glucose composition was prepared by diluting the concentrates. Further, the glucose composition was adjusted to a final pH of 7 using 6 N sodium hydroxide.

To 9 mL of the prepared glucose composition, 1 mL of a 20% CSL (manufactured by Oji Cornstarch Co., Ltd., after the pH was adjusted to 5 with 1 N NaOH, filter sterilization was performed through a filter with an average pore diameter of 0.45 μm) solution was added as a nitrogen source, and the precultured bacterial cells described in Reference Example 11 were inoculated therein to an initial OD of 0.5. This was subjected to reciprocal shaking culture with an inclination of 50° at 30° C. and 120 rpm for 144 hours. Sampling was performed about every 24 hours, and the sugar concentration and the ethanol concentration were analyzed, and the maximum fermentation rate and the fermentation yield versus the theoretical ratio (the theoretical ratio when the theoretical yield of ethanol was assumed to be 0.51 g/g—the total consumed sugar) were determined. As the evaluation of microbial growth potential, the OD (OD600) of the culture solution after 48-hour culture was measured. The results are shown in Table 11.

Example 47: Preparation of Glucose Composition and Ethanol Fermentation Production The same procedure as in Example 46 was performed except that a glucose composition containing 100 g/L of glucose, 0.7 g/L of xylose, 0.1 g/L of acetic acid, 0.15 g/L of coumaric acid, and 0.007 g/L of ferulic acid was prepared. The results are shown in Table 11.

Example 48: Preparation of Glucose Composition and Ethanol Fermentation Production The same procedure as in Example 46 was performed except that a glucose composition containing 100 g/L of glucose, 22.3 g/L of xylose, 1.0 g/L of acetic acid, 0.5 g/L of coumaric acid, and 0.06 g/L of ferulic acid was prepared. The results are shown in Table 11.

Example 49: Preparation of Glucose Composition and Ethanol Fermentation Production The same procedure as in Example 46 was performed except that a glucose composition containing 100 g/L of glucose, 25 g/L of xylose, 10 g/L of acetic acid, 2.0 g/L of coumaric acid, and 0.28 g/L of ferulic acid was prepared. The results are shown in Table 11.

Comparative Example 41: Comparative Example of Glucose Composition in Ethanol Fermentation Production The same procedure as in Example 46 was performed except that a glucose composition containing only 100 g/L of glucose was prepared. The results are shown in Table 11.

Comparative Example 42: Comparative Example of Glucose Composition in Ethanol Fermentation Production The same procedure as in Example 46 was performed except that a glucose composition containing 100 g/L of glucose, 22.3 g/L of xylose, 15 g/L of acetic acid, 0.5 g/L of coumaric acid, and 0.06 g/L of ferulic acid was prepared. The results are shown in Table 11.

Comparative Example 43: Comparative Example of Glucose Composition in Ethanol Fermentation Production The same procedure as in Example 46 was performed except that a glucose composition containing 100 g/L of glucose, 22.3 g/L of xylose, no acetic acid, 0.5 g/L of coumaric acid, and 0.06 g/L of ferulic acid was prepared. The results are shown in Table 11.

Comparative Example 44: Comparative Example of Glucose Composition in Ethanol Fermentation Production The same procedure as in Example 46 was performed except that a glucose composition containing 100 g/L of glucose, 22.3 g/L of xylose, 1.0 g/L of acetic acid, 3.0 g/L of coumaric acid, and 0.06 g/L of ferulic acid was prepared. The results are shown in Table 11.

Comparative Example 45: Comparative Example of Glucose Composition in Ethanol Fermentation Production The same procedure as in Example 46 was performed except that a glucose composition containing 100 g/L of glucose, 22.3 g/L of xylose, 1.0 g/L of acetic acid, no coumaric acid, and 0.06 g/L of ferulic acid was prepared. The results are shown in Table 11.

Comparative Example 46: Comparative Example of Glucose Composition in Ethanol Fermentation Production The same procedure as in Example 46 was performed except that a glucose composition containing 100 g/L of glucose, 22.3 g/L of xylose, 1.0 g/L of acetic acid, 0.5 g/L of coumaric acid, and 0.4 g/L of ferulic acid was prepared. The results are shown in Table 11.

Comparative Example 47: Comparative Example of Glucose Composition in Ethanol Fermentation Production The same procedure as in Example 46 was performed except that a glucose composition containing 100 g/L of glucose, 22.3 g/L of xylose, 1.0 g/L of acetic acid, 0.5 g/L of coumaric acid, and no ferulic acid was prepared. The results are shown in Table 11.

Comparative Example 48: Comparative Example of Glucose Composition in Ethanol Fermentation Production The same procedure as in Example 46 was performed except that a glucose composition containing 100 g/L of glucose, 50 g/L of xylose, 1.0 g/L of acetic acid, 0.5 g/L of coumaric acid, and 0.06 g/L of ferulic acid was prepared. The results are shown in Table 11.

TABLE 11

Ethanol fermentation test results using each glucose composition as fermentation raw material

| | Concentration in glucose composition (at the time of preparation) | | | | | Fermentation properties | | |
|---|---|---|---|---|---|---|---|---|
| | Glucose (g/L) | Xylose (g/L) | Acetic acid (g/L) | Coumaric acid (g/L) | Ferulic acid (g/L) | Microbial growth potential (O.D. 600 after 48 h) | Fermentation rate (g/L/h) | Fermentation yield versus theoretical ratio (%) |
| Example 46 | 100 | 0 | 0.1 | 0.15 | 0.007 | 13.5 | 1.3 | 89 |
| Example 47 | 100 | 0.7 | 0.1 | 0.15 | 0.007 | 12.5 | 1.3 | 89 |
| Example 48 | 100 | 22.3 | 1.0 | 0.5 | 0.06 | 10.3 | 1.3 | 92 |
| Example 49 | 100 | 25.0 | 10.0 | 2.0 | 0.28 | 10.2 | 1.2 | 91 |
| Comparative Example 41 | 100 | 0 | 0 | 0 | 0 | 13.8 | 1.1 | 82 |
| Comparative Example 42 | 100 | 22.3 | 15 | 0.5 | 0.06 | 9.2 | 1.1 | 78 |
| Comparative Example 43 | 100 | 22.3 | 0 | 0.5 | 0.06 | 12.2 | 1.0 | 81 |
| Comparative Example 44 | 100 | 22.3 | 1.0 | 3.0 | 0.06 | 9.5 | 1.0 | 79 |
| Comparative Example 45 | 100 | 22.3 | 1.0 | 0 | 0.06 | 11.8 | 1.0 | 82 |
| Comparative Example 46 | 100 | 22.3 | 1.0 | 0.5 | 0.4 | 9.2 | 0.9 | 77 |
| Comparative Example 47 | 100 | 22.3 | 1.0 | 0.5 | 0 | 11.0 | 1.0 | 82 |
| Comparative Example 48 | 100 | 50 | 1.0 | 0.5 | 0.06 | 9.8 | 1.1 | 85 |

Example 50: Preparation of Glucose Composition Using Cellulose-Containing Biomass as Raw Material and Ethanol Fermentation Production By using the glucose composition shown in Example 5, ethanol fermentation was performed in the same manner as in Example 46. The results are shown in Table 12.

Example 51: Preparation of Glucose Composition Using Cellulose-Containing Biomass as Raw Material and Ethanol Fermentation Production By using the glucose composition shown in Example 6, ethanol fermentation was performed in the same manner as in Example 46. The results are shown in Table 12.

Example 52: Preparation of Glucose Composition Using Cellulose-Containing Biomass as Raw Material and Ethanol Fermentation Production By using the glucose composition shown in Example 7, ethanol fermentation was performed in the same manner as in Example 46. The results are shown in Table 12.

Example 53: Preparation of Glucose Composition Using Cellulose-Containing Biomass as Raw Material and Ethanol Fermentation Production By using the glucose composition shown in Example 8, ethanol fermentation was performed in the same manner as in Example 46. The results are shown in Table 12.

Example 54: Preparation of Glucose Composition Using Cellulose-Containing Biomass as Raw Material and Ethanol Fermentation Production By using the glucose composition shown in Example 9, ethanol fermentation was performed in the same manner as in Example 46. The results are shown in Table 12.

INDUSTRIAL APPLICABILITY

The glucose composition is not only useful as a microbial fermentation raw material to produce a chemical product by microbial fermentation, but also can be used for various applications of known glucose compositions.

The invention claimed is:

1. A glucose composition containing 0.5 to 25 g/L of xylose, 1.0 to 10 g/L of acetic acid, 0.3 to 2.0 g/L of coumaric acid, 0.007 to 0.28 g/L of ferulic acid, and a substance obtained by subjecting bagasse to an alkali treatment having an absorption at 280 nm measured in a 1-cm width cell at a concentration defined by an absorbance (ABS) of 20 to 350, as equivalents in an aqueous solution of the composition having a glucose concentration of 100 g/L.

2. A glucose composition for a microbial fermentation, containing the glucose composition according to claim 1.

3. A microbial fermentation raw material containing the glucose composition of claim 1.

4. A method of producing a chemical product, comprising culturing a microorganism having an ability to produce the chemical product by using the microbial fermentation raw material according to claim 3.

5. The glucose composition according to claim 1, wherein the content of acetic acid is 1.0 to 4 g/L, as equivalents in an aqueous solution of the composition having a glucose concentration of 100 g/L.

6. The glucose composition according to claim 1, wherein the content of ferulic acid is 0.014 to 0.14 g/L, as equivalents in an aqueous solution of the composition having a glucose concentration of 100 g/L.

7. The glucose composition according to claim 1, wherein the content of coumaric acid is 0.3 to 1.0 g/L, as equivalents in an aqueous solution of the composition having a glucose concentration of 100 g/L.

8. The glucose composition according to claim 1, wherein the content of coumaric acid is 0.3 to 0.5 g/L, as equivalents in an aqueous solution of the composition having a glucose concentration of 100 g/L.

TABLE 12

Ethanol fermentation test results using each glucose composition as fermentation raw material

| | Concentration in glucose composition (at the time of preparation) | | | | | | Fermentation properties | | |
| --- | --- | --- | --- | --- | --- | --- | --- | --- | --- |
| | Glucose (g/L) | Xylose (g/L) | Acetic acid (g/L) | Coumaric acid (g/L) | Ferulic acid (g/L) | Absorbance (ABS) at 280 nm | Microbial growth potential (O.D. 600 after 48 h) | Fermentation rate (g/L/h) | Fermentation yield versus theoretical ratio (%) |
| Example 50 | 100 | 22.3 | 1.0 | 0.5 | 0.06 | 128 | 9.7 | 1.6 | 95 |
| Example 51 | 100 | 22.3 | 1.0 | 0.5 | 0.06 | 12 | 10.2 | 1.4 | 94 |
| Example 52 | 100 | 22.3 | 1.0 | 0.5 | 0.06 | 20 | 10.2 | 1.5 | 96 |
| Example 53 | 100 | 22.3 | 1.0 | 0.5 | 0.06 | 350 | 9.8 | 1.6 | 95 |
| Example 54 | 100 | 22.3 | 1.0 | 0.5 | 0.06 | 1040 | 9.2 | 1.4 | 91 |
| Comparative Example 41 | 100 | 0 | 0 | 0 | 0 | 0 | 13.8 | 1.1 | 82 |

9. The glucose composition according to claim 1, wherein the coumaric acid comprises a trans-p-coumaric acid.

\* \* \* \* \*